United States Patent
Fukuda et al.

(10) Patent No.: US 8,173,649 B2
(45) Date of Patent: *May 8, 2012

(54) GLUCOKINASE ACTIVATOR

(75) Inventors: Yasumichi Fukuda, Tochigi (JP);
Yoshikazu Asahina, Tochigi (JP);
Ayako Nakamura, Tochigi (JP); Kenji Fujita, Kanagawa (JP); Tomohiro Ide, Tochigi (JP); Fumiyoshi Kobayashi, Tochigi (JP); Shinji Kobayashi, Tokyo (JP); Kanji Komatsu, Tokyo (JP); Masanori Yamamoto, Tokyo (JP)

(73) Assignees: Kyorin Pharmaceutical Co., Ltd., Tokyo (JP); Teijin Pharma Limited, Tokyo (JP)

( * ) Notice: Subject to any disclaimer, the term of this patent is extended or adjusted under 35 U.S.C. 154(b) by 226 days.

This patent is subject to a terminal disclaimer.

(21) Appl. No.: 12/448,549

(22) PCT Filed: Dec. 21, 2007

(86) PCT No.: PCT/JP2007/074638
§ 371 (c)(1),
(2), (4) Date: Aug. 31, 2009

(87) PCT Pub. No.: WO2008/078674
PCT Pub. Date: Jul. 3, 2008

(65) Prior Publication Data
US 2010/0016304 A1   Jan. 21, 2010

(30) Foreign Application Priority Data

Dec. 25, 2006 (JP) .................................. 2006-348222
Mar. 7, 2007 (JP) .................................. 2007-057427

(51) Int. Cl.
A61K 31/5377 (2006.01)
A61K 31/421 (2006.01)
A61K 31/426 (2006.01)
A61K 31/4365 (2006.01)
C07D 263/14 (2006.01)
C07D 277/28 (2006.01)
C07D 513/04 (2006.01)
C07D 417/12 (2006.01)
A61P 3/10 (2006.01)

(52) U.S. Cl. .................. 514/233.8; 514/301; 514/371; 514/376; 544/135; 546/114; 548/195; 548/230

(58) Field of Classification Search .................. None
See application file for complete search history.

(56) References Cited

U.S. PATENT DOCUMENTS

| | | |
|---|---|---|
| 6,353,111 B1 | 3/2002 | Corbett et al. |
| 6,369,232 B1 | 4/2002 | Sidduri |
| 6,384,220 B2 | 5/2002 | Corbett et al. |
| 6,388,071 B2 | 5/2002 | Mahaney |
| 6,388,088 B1 | 5/2002 | Sidduri |
| 6,433,188 B1 | 8/2002 | Corbett et al. |
| 6,441,180 B1 | 8/2002 | Sidduri |
| 6,441,184 B1 | 8/2002 | Corbett et al. |
| 6,448,399 B1 | 9/2002 | Corbett et al. |
| 6,482,951 B2 | 11/2002 | Guertin |
| 6,486,184 B2 | 11/2002 | Kester et al. |
| 6,489,485 B2 | 12/2002 | Bizzarro et al. |
| 6,528,543 B1 | 3/2003 | Bizzarro et al. |
| 6,545,155 B2 | 4/2003 | Corbett et al. |
| 6,583,288 B2 | 6/2003 | Goodnow, Jr. et al. |
| 6,608,218 B2 | 8/2003 | Kester et al. |
| 6,784,298 B2 | 8/2004 | Goodnow, Jr. et al. |
| 6,911,545 B2 | 6/2005 | Corbett et al. |
| 7,105,671 B2 | 9/2006 | Corbett et al. |
| 7,262,196 B2 | 8/2007 | Fyfe et al. |
| 8,034,819 B2 * | 10/2011 | Fukuda et al. ............ 514/255.06 |

(Continued)

FOREIGN PATENT DOCUMENTS

EP    1 921 074    5/2008

(Continued)

OTHER PUBLICATIONS

U.S. Appl. No. 12/448,549, filed Aug. 31, 2009.

(Continued)

*Primary Examiner* — Kamal Saeed
(74) *Attorney, Agent, or Firm* — Wenderoth Lind & Ponack, L.L.P.

(57) ABSTRACT

A compound represented by the following formula (1):

(Chemical formula 1)

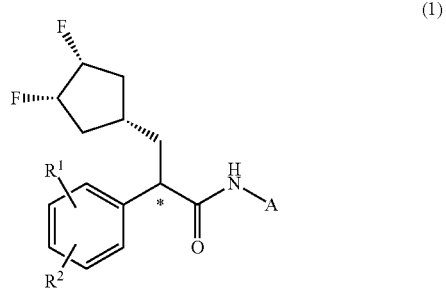

(1)

(wherein the carbon atom denoted by * is in the R-configuration; $R^1$ and $R^2$ are each independently a hydrogen atom, a halogen atom, an amino group, a hydroxyl group, a hydroxyamino group, a nitro group, a cyano group, a sulfamoyl group, a $C_1$-$C_6$ alkyl group, a $C_1$-$C_6$ alkoxy group, a $C_1$-$C_6$ alkylsulfanyl group, a $C_1$-$C_6$ alkylsulfinyl group or a $C_1$-$C_6$ alkylsulfonyl group; and A is a substituted or unsubstituted heteroaryl group), or a pharmaceutically acceptable salt thereof.

30 Claims, No Drawings

U.S. PATENT DOCUMENTS

| | | |
|---|---|---|
| 2001/0051731 A1 | 12/2001 | Bizzarro et al. |
| 2001/0053851 A1 | 12/2001 | Mahaney |
| 2001/0056191 A1 | 12/2001 | Goodnow, Jr. et al. |
| 2002/0002190 A1 | 1/2002 | Corbett et al. |
| 2002/0035266 A1 | 3/2002 | Sidduri |
| 2002/0035267 A1 | 3/2002 | Sidduri |
| 2002/0042512 A1 | 4/2002 | Kester et al. |
| 2002/0065275 A1 | 5/2002 | Sidduri |
| 2002/0082260 A1 | 6/2002 | Guertin |
| 2002/0103199 A1 | 8/2002 | Corbett et al. |
| 2002/0103241 A1 | 8/2002 | Corbett et al. |
| 2002/0107396 A1 | 8/2002 | Corbett et al. |
| 2002/0111372 A1 | 8/2002 | Corbett et al. |
| 2002/0198200 A1 | 12/2002 | Kester et al. |
| 2003/0060625 A1 | 3/2003 | Bizzarro et al. |
| 2003/0225283 A1 | 12/2003 | Corbett et al. |
| 2003/0225286 A1 | 12/2003 | Goodnow, Jr. et al. |
| 2003/0235551 A1 | 12/2003 | Pagilagan |
| 2004/0147748 A1 | 7/2004 | Chen et al. |
| 2004/0181067 A1 | 9/2004 | Fyfe et al. |
| 2004/0186290 A1 | 9/2004 | Fyfe et al. |
| 2005/0282851 A1 | 12/2005 | Bebernitz |
| 2006/0141599 A1 | 6/2006 | Corbett et al. |
| 2006/0178429 A1 | 8/2006 | Corbett et al. |
| 2007/0129554 A1 | 6/2007 | Harrington et al. |
| 2007/0265297 A1 | 11/2007 | Bebernitz et al. |
| 2008/0009465 A1 | 1/2008 | Ryono et al. |
| 2008/0015358 A1 | 1/2008 | Fyfe et al. |
| 2008/0021032 A1 | 1/2008 | Berthel et al. |
| 2008/0021052 A1 | 1/2008 | Chen et al. |
| 2008/0103167 A1 | 5/2008 | Bebernitz et al. |
| 2008/0139562 A1 | 6/2008 | Jeppesen et al. |
| 2008/0242869 A1 | 10/2008 | Fyfe |
| 2008/0293730 A1 | 11/2008 | Fyfe et al. |
| 2008/0293741 A1 | 11/2008 | Fyfe et al. |
| 2008/0312256 A1 | 12/2008 | Bebernitz et al. |
| 2008/0318948 A1 | 12/2008 | Bebernitz |
| 2009/0005391 A1 | 1/2009 | Fyfe et al. |
| 2009/0054444 A1 | 2/2009 | Fyfe et al. |
| 2010/0016304 A1 | 1/2010 | Fukuda et al. |
| 2010/0099671 A1* | 4/2010 | Fukuda et al. ............ 514/233.8 |
| 2011/0160211 A1 | 6/2011 | Fukuda et al. |

FOREIGN PATENT DOCUMENTS

| | | |
|---|---|---|
| WO | 02/46173 | 6/2002 |
| WO | 03/095438 | 11/2003 |
| WO | 2004/052869 | 6/2004 |
| WO | 2004/063194 | 7/2004 |
| WO | 2005/103021 | 11/2005 |
| WO | 2006/016178 | 2/2006 |
| WO | 2006/059163 | 6/2006 |
| WO | 2008/012227 | 1/2008 |

OTHER PUBLICATIONS

U.S. Appl. No. 12/989,838, filed Nov. 24, 2010.

International Search Report dated Mar. 11, 2008 in the International (PCT) Application PCT/JP2007/074638 of which the present application is the U.S. National Stage.

* cited by examiner

GLUCOKINASE ACTIVATOR

TECHNICAL FIELD

The present invention relates to activators of glucokinase (which may be referred to simply as GK, hereinafter). The present invention also relates to a pharmaceutical composition containing a GK activator as an active ingredient suitable for the treatment or prevention of diabetes, obesity and other disorders.

BACKGROUND ART

A 2002 patient survey conducted by the Ministry of Health, Labor, and Welfare of Japan revealed that the total number of patients with diabetes was 2,280,000 in Japan. A diabetes research conducted in the same year estimated that the number of patients strongly suspected of having diabetes and the number of patients for whom the possibility of diabetes could not be denied add up to 16,200,000.

As far as the domestic market is concerned, Japanese have a genetic factor for decreased insulin secretion and, thus, defective insulin secretion predominates. However, an increasing number of patients are suffering from insulin resistance due to the recent shift to western diets. Thus, there is a need for drugs that are effective against both defective insulin secretion and insulin resistance.

Glucokinase (GK) is an enzyme that catalyzes phosphorylation of glucose. The enzyme acts as a glucose sensor in the body by promoting insulin secretion and glucose utilization in liver in response to high glucose levels. Since whole-body glucose homeostasis is not maintained in diabetic patients, activation of GK in these patients can reduce the blood glucose levels by facilitating glucose-dependent insulin secretion in pancreas and by facilitating glucose utilization in the liver or suppressing glucose release from the liver (dual action) (Non-Patent Documents 1 through 3). Effective against both defective insulin secretion (pancreatic action) and insulin resistance (hepatic action), GK activators are considered an ideal treatment for diabetes.

Among known GK activators are a variety of amide compounds (Patent Documents 11 through 19), including arylcycloalkylpropionamides (Patent Document 1), 2,3-disubstituted trans olefinic N-heteroaromatic ring- or ureidopropionamides (Patent Document 2), alkynylphenyl heteroaromatic amides (Patent Document 3), hydantoins (Patent Document 4), substituted phenylacetamides (Patent Document 5), para-alkyl-, alyl, cycloheteroalkyl-, or heteroaryl-(carbonyl or sulfonyl)amine-substituted phenylamides (Patent Document 6), alpha-acyl and alpha-heteroatom substituted benzeneacetamides (Patent Document 7), tetrazolyl phenylacetamides (Patent Document 8), fused heteroaromatic compounds (Patent Document 9), and phenylacetamides having a cycloalkane with a single carbon atom substituted or a heterocyclic ring (Patent Document 10). However, no reports have described GK activators in which two fluorine atoms are attached to different carbon atoms of a cyclopentyl group.

Patent Document 1 WO2000/058293 pamphlet
Patent Document 2 WO2001/044216 pamphlet
Patent Document 3 WO2001/083465 pamphlet
Patent Document 4 WO2001/083478 pamphlet
Patent Document 5 WO2001/085706 pamphlet
Patent Document 6 WO2001/085707 pamphlet
Patent Document 7 WO2002/008209 pamphlet
Patent Document 8 WO2002/014312 pamphlet
Patent Document 9 WO2002/046173 pamphlet
Patent Document 10 WO2003/095438 pamphlet
Patent Document 11 WO2004/052869 pamphlet
Patent Document 12 WO2004/072031 pamphlet
Patent Document 13 WO2004/072066 pamphlet
Patent Document 14 WO2005/103021 pamphlet
Patent Document 15 WO2006/016174 pamphlet
Patent Document 16 WO2006/016178 pamphlet
Patent Document 17 WO2006/016194 pamphlet
Patent Document 18 WO2006/059163 pamphlet
Patent Document 19 U.S. Pat. No. 6,911,545
Non-Patent Document 1 *Diabetes* 45, 223-241 (1996)
Non-Patent Document 2 *Diabetes* 41, 792-806 (1992)
Non-Patent Document 3 *FASEB J.* 10, 1213-1218 (1996)

DISCLOSURE OF THE INVENTION

Problems to be Solved by the Invention

Accordingly, it is an object of the present invention to provide compounds that act as effective GK activators or hypoglycemic agents and are useful in the treatment or prevention of diabetes, obesity and other disorders.

Means for Solving the Problems

In the course of the inventors' study to find ways to achieve the foregoing object, the present inventors have found that, among propionamide compounds having 3,4-difluorocyclopentyl group at position 3, those with specific stereostructure act as effective GK activators or hypoglycemic agents. It is this discovery that ultimately led to the present invention.

Specifically, the present invention concerns the following:
1) A compound represented by the following general formula (1), or a pharmaceutically acceptable salt thereof:

(Chemical formula 1)

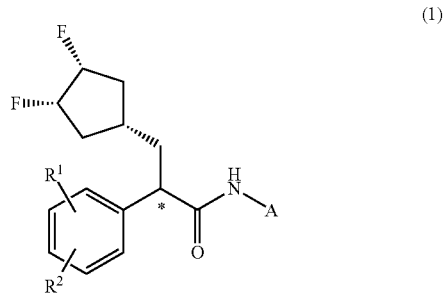

(1)

(wherein the carbon atom denoted by * is in the R-configuration; $R^1$ and $R^2$ are each independently a hydrogen atom, a halogen atom, an amino group, a hydroxyl group, a hydroxyamino group, a nitro group, a cyano group, a sulfamoyl group, a $C_1$-$C_6$ alkyl group, a $C_1$-$C_6$ alkoxy group, a $C_1$-$C_6$ alkylsulfanyl group, a $C_1$-$C_6$ alkylsulfinyl group, or a $C_1$-$C_6$ alkylsulfonyl group; and A is a substituted or unsubstituted heteroaryl group).

2) The compound according to 1), or a pharmaceutically acceptable salt thereof, wherein $R^1$ is a hydrogen atom and $R^2$ is a $C_1$-$C_6$ alkylsulfonyl group.

3) The compound according to 1), or a pharmaceutically acceptable salt thereof, wherein $R^1$ is a hydrogen atom and $R^2$ is a methylsulfonyl group.

4) The compound according to any of 1) to 3) represented by the following general formula (1a), or a pharmaceutically acceptable salt thereof:

(Chemical formula 2)

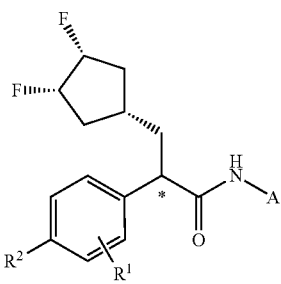

(1a)

(wherein *, $R^1$, $R^2$ and A are as defined above).

5) The compound according to any of 1) to 3) represented by the following general formula (1b), or a pharmaceutically acceptable salt thereof:

(Chemical formula 3)

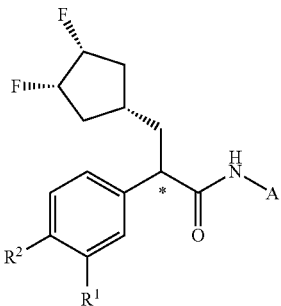

(1b)

(wherein *, $R^1$, $R^2$ and A are as defined above).

6) The compound according to any of 1) to 5), or a pharmaceutically acceptable salt thereof, wherein A is a heteroaryl group that is unsubstituted or monosubstituted with a halogen atom, a $C_1$-$C_6$ alkyl group, a $C_1$-$C_6$ alkoxy group, a nitro group, a cyano group or —$(CH_2)_m C(O)OR^3$ (wherein $R^3$ is a hydrogen atom or a $C_1$-$C_6$ alkyl group, and m is an integer of 0 to 2).

7) The compound according to any of 1) to 5), or a pharmaceutically acceptable salt thereof, wherein A is a heteroaryl group unsubstituted or monosubstituted with a halogen atom or a $C_1$-$C_6$ alkyl group.

8) The compound according to 6) or 7), or a pharmaceutically acceptable salt thereof, wherein A is a unsubstituted or monosubstituted heteroaryl group which is a 5- or 6-membered aromatic heterocyclic ring that contains 1 to 3 heteroatoms selected from a sulfur atom, an oxygen atom and a nitrogen atom, one of which is a nitrogen atom adjacent to the ring-linking atom.

9) The compound according to 6) or 7), or a pharmaceutically acceptable salt thereof, wherein A is a unsubstituted or monosubstituted heteroaryl group which is a fused heterocyclic ring containing a 5- or 6-membered aromatic heterocyclic ring that contains 1 to 3 heteroatoms selected from a sulfur atom, an oxygen atom and a nitrogen atom, one of which is a nitrogen atom adjacent to the ring-linking atom.

10) The compound according to 6) or 7), or a pharmaceutically acceptable salt thereof, wherein A is a unsubstituted or substituted heteroaryl group which is selected from the following:

(Chemical formula 4)

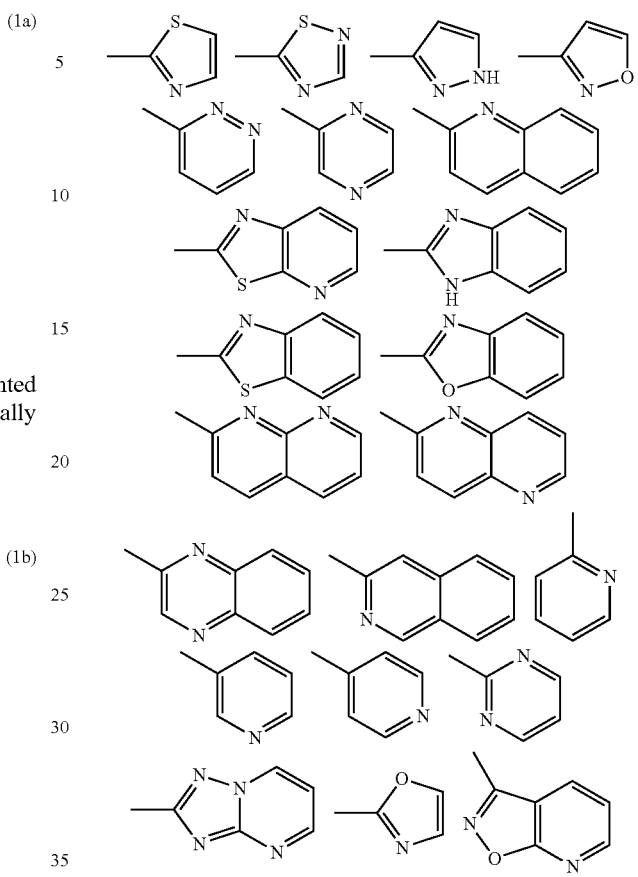

11) (R)-3-((1r,3R,4S)-3,4-difluorocyclopentyl)-2-(4-(methylsulfonyl)phenyl)-N-(thiazole-2-yl)propionamide, (R)-3-((1r,3R,4S)-3,4-difluorocyclopentyl)-2-(4-(methylsulfonyl)phenyl)-N-(5-fluorothiazole-2-yl)propionamide, (R)-3-((1r,3R,4S)-3,4-difluorocyclopentyl)-2-(4-(methylsulfonyl)phenyl)-N-(1-methylpyrazole-3-yl)propionamide, (R)-3-((1r,3R,4S)-3,4-difluorocyclopentyl)-2-(4-(methylsulfonyl)phenyl)-N-(pyrido[3,2-d]thiazole-2-yl)propionamide or (R)-3-((1r,3R,4S)-3,4-difluorocyclopentyl)-2-(4-(methylsulfonyl)phenyl)-N-(3-methylthiadiazole-5-yl)propionamide, or pharmaceutically acceptable salts thereof.

12) (−)-3-[(1α,3α,4α)-3,4-difluorocyclopentyl]-2-(4-(methylsulfonyl)phenyl)-N-(thiazole-2-yl)propionamide represented by the following formula (2):

(Chemical formula 5)

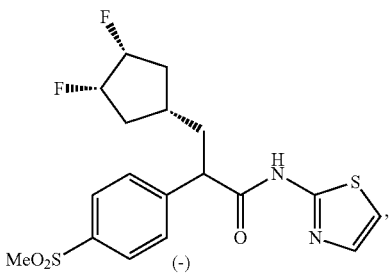

(2)

or a pharmaceutically acceptable salt thereof.

13) (−)-3-[(1α,3α,4α)-3,4-difluorocyclopentyl]-2-(4-(methylsulfonyl)phenyl)-N-(5-fluorothiazole-2-yl)propionamide, or a pharmaceutically acceptable salt thereof.

14) (−)-3-[(1α,3α,4α)-3,4-difluorocyclopentyl]-2-(4-(methylsulfonyl)phenyl)-N-(1-methylpyrazole-3-yl)propionamide, or a pharmaceutically acceptable salt thereof.

15) (−)-3-[(1α,3α,4α)-3,4-difluorocyclopentyl]-2-(4-(methylsulfonyl)phenyl)-N-(pyrido[3,2-d]thiazole-2-yl)propionamide, or a pharmaceutically acceptable salt thereof.

16) (−)-3-[(1α,3α,4α)-3,4-difluorocyclopentyl]-2-(4-(methylsulfonyl)phenyl)-N-(3-methylthiadiazole-5-yl)propionamide, or a pharmaceutically acceptable salt thereof.

17) A method of treating or preventing diabetes, comprising administering the compound according to any of claims 1-16 or a pharmaceutically acceptable salt thereof.

18) Use of the compound according to any one of claims 1 to 16 or a pharmaceutically acceptable salt thereof in the manufacture of a medicament for the treatment or prevention of diabetes.

19) A pharmaceutical composition comprising the compound according to any one of claims 1 to 16 or a pharmaceutically acceptable salt thereof and a pharmaceutically acceptable carrier.

20) A compound represented by the following general formula (3):

(Chemical formula 6)

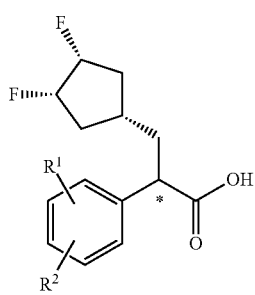

(3)

(wherein the carbon atom denoted by * is in the R-configuration; $R^1$ and $R^2$ are each independently a hydrogen atom, a halogen atom, an amino group, a hydroxyl group, a hydroxyamino group, a nitro group, a cyano group, a sulfamoyl group, a $C_1$-$C_6$ alkyl group, a $C_1$-$C_6$ alkoxy group, a $C_1$-$C_6$ alkylsulfanyl group, a $C_1$-$C_6$ alkylsulfinyl group or a $C_1$-$C_6$ alkylsulfonyl group).

21) The compound according to 20), wherein $R^1$ is a hydrogen atom and $R^2$ is a methylsulfonyl group.

Effect of the Invention

According to the present invention, there is provided a compound that acts as an effective GK activator or hypoglycemic agent and causes fewer (less) side effects (such as prolongation of QT interval and hypoglycemia), as well as a pharmaceutical composition useful in the treatment or prevention of diabetes, obesity and other disorders.

BEST MODE FOR CARRYING OUT THE INVENTION

As used herein, the term "halogen atom" refers to a fluorine atom, a chlorine atom, a bromine atom, or an iodine atom.

As used herein, the term "$C_1$-$C_6$ alkyl group" refers to a straight or branched alkyl group having 1 to 6 carbon atoms, or a cycloalkyl group having 3 to 6 carbon atoms, such as a methyl group, an ethyl group, a propyl group, an isopropyl group, a butyl group, an isobutyl group, a sec-butyl group, a tert-butyl group, a cyclopropyl group, and a cyclobutyl group.

As used herein, the term "$C_1$-$C_6$ alkoxy group" refers to a straight or branched alkoxy group having 1 to 6 carbon atoms, or a cycloalkoxy group having 3 to 6 carbon atoms, such as a methoxy group, an ethoxy group, a propoxy group, an isopropoxy group, a butoxy group, an isobutoxy group, a sec-butoxy group, a tert-butoxy group, a cyclopropoxy group, and a cyclobutoxy group.

As used herein, the term "$C_1$-$C_6$ alkylsulfanyl" refers to a straight or branched alkylsulfanyl group having 1 to 6 carbon atoms, such as a methylsulfanyl group, an ethylsulfanyl group, a propylsulfanyl group, an isopropylsulfanyl group, a butylsulfanyl group, an isobutylsulfanyl group, a sec-butylsulfanyl group, and a tert-butylsulfanyl group As used herein, the term "$C_1$-$C_6$ alkylsulfinyl" refers to a straight or branched alkylsulfinyl group having 1 to 6 carbon atoms, such as a methylsulfinyl group, an ethylsulfinyl group, a propylsulfinyl group, an isopropylsulfinyl group, a butylsulfinyl group, an isobutylsulfinyl group, a sec-butylsulfinyl group, and a tert-butylsulfinyl group.

As used herein, the term "$C_1$-$C_6$ alkylsulfonyl" refers to a straight or branched alkylsulfonyl group having 1 to 6 carbon atoms, such as a methylsulfonyl group, an ethylsulfonyl group, a propylsulfonyl group, an isopropylsulfonyl group, a butylsulfonyl group, an isobutylsulfonyl group, a sec-butylsulfonyl group, and a tert-butylsulfonyl group.

As used herein, the term "heteroaryl group" refers to a 5- or 6-membered aromatic heterocyclic ring that contains 1 to 3 heteroatoms selected from a sulfur atom, an oxygen atom, and a nitrogen atom and may form a fused ring with a benzene ring or a 5- or 6-membered aromatic heterocyclic ring. A preferred heteroaryl group is one that contains 1 to 3 heteroatoms selected from a sulfur atom, an oxygen atom, and a nitrogen atom, one of which is a nitrogen atom adjacent to the ring-linking atom. The term "ring-linking atom" as used herein refers to one of the members of the heterocyclic ring that binds to the nitrogen atom of the amide group. The ring-linking atom is preferably a carbon atom.

Examples of preferred heteroaryl groups include a thiazolyl group, a thiadiazolyl group, a pyrazolyl group, a pyridinyl group, a pyrazinyl group, a pyrimidinyl group, a pyridazinyl group, an oxazolyl group, an imidazolyl group, a triazinyl group, a benzothiazolyl group, a benzoxazolyl group, a benzimidazolyl group, a pyridothiazolyl group, and a quinolinyl group. Of these, a thiazolyl group, a pyridinyl group, a pyrazinyl group, a pyrazolyl group, a thiadiazolyl group, and a pyridothiazolyl group are particularly preferred.

The substituted or unsubstituted heteroaryl group denoted by A is preferably an unsubstituted or monosubstituted heteroaryl group. The substituent may be a halogen atom, a $C_1$-$C_6$ alkyl group, a $C_1$-$C_6$ alkoxy group, a nitro group, a cyano group and a group represented by —$(CH_2)_mC(O)OR^3$ (wherein $R^3$ is a hydrogen atom or a $C_1$-$C_6$ alkyl group, and m is an integer of 0 to 2).

Having the above-described stereostructure, the compounds of the present invention act as effective GK activators. When A is a heteroaryl group unsubstituted or monosubstituted with a halogen atom or a $C_1$-$C_6$ alkyl group, the compounds show favorable pharmacokinetics and are effectively transferred into the blood, acting as an effective hypoglycemic agent. As will be described later, compounds that differ from the compounds of the present invention in their stereostructure with respect to the cyclopentyl group and the fluorine atoms bound to it and/or the configuration of the carbon atom denoted by * (e.g., (+)-3-[(1α,3α,4α)-3,4-difluorocyclopentyl]-2-(4-(methylsulfonyl)phenyl)-N-(thiazole-2-yl)propionamide (S-configuration), (−)-3-[(1α,3α,4α)-3,4-difluorocyclopentyl]-2-(4-(methylsulfonyl)phenyl)-N-(thiazole-2-yl)propionamide, and (+)-3-[(1α,3α,4α)-3,4-difluorocyclopentyl]-2-(4-(methylsulfonyl)phenyl)-N-(thiazole-2-yl)propionamide) do not exhibit high hypoglycemic activity.

Unless otherwise specified, what the expression "optical rotation (−)" means is that the optical rotation of the compound as determined by the sodium D line using chloroform as a solvent is negative (−).

It should be noted that (−)-3-[(1α,3α,4α)-3,4-difluorocyclopentyl]-2-(4-(methylsulfonyl)phenyl)-N-(thiazole-2-yl)propionamide may also be named as (R)-3-[(1α,3α,4α)-3,4-difluorocyclopentyl]-2-(4-(methylsulfonyl)phenyl)-N-(thiazole-2-yl)propionamide or (R)-3-((1r,3R,4S)-3,4-difluorocyclopentyl)-2-(4-(methylsulfonyl)phenyl)-N-(thiazole-2-yl)propionamide. (−)-3-[(1α,3α,4α)-3,4-difluorocyclopentyl]-2-(4-(methylsulfonyl)phenyl)-N-(5-fluorothiazole-2-yl)propionamide may also be named as (R)-3-[(1α,3α,4α)-3,4-difluorocyclopentyl]-2-(4-(methylsulfonyl)phenyl)-N-(5-fluorothiazole-2-yl)propionamide or (R)-3-((1r,3R,4S)-3,4-difluorocyclopentyl)-2-(4-(methylsulfonyl)phenyl)-N-(5-fluorothiazole-2-yl)propionamide. (−)-3-[(1α,3α,4α)-3,4-difluorocyclopentyl]-2-(4-(methylsulfonyl)phenyl)-N-(1-methylpyrazole-3-yl)propionamide may also be named as (R)-3-[(1α,3α,4α)-3,4-difluorocyclopentyl]-2-(4-(methylsulfonyl)phenyl)-N-(1-methylpyrazole-3-yl)propionamide or (R)-3-((1r,3R,4S)-3,4-difluorocyclopentyl)-2-(4-(methylsulfonyl)phenyl)-N-(1-methylpyrazole-3-yl)propionamide. (−)-3-[(1α,3α,4α)-3,4-difluorocyclopentyl]-2-(4-(methylsulfonyl)phenyl)-N-(pyrido[3,2-d]thiazole-2-yl)propionamide may also be named as (R)-3-[(1α,3α,4α)-3,4-difluorocyclopentyl]-2-(4-(methylsulfonyl)phenyl)-N-(pyrido[3,2-d]thiazole-2-yl)propionamide or (R)-3-((1r,3R,4S)-3,4-difluorocyclopentyl)-2-(4-(methylsulfonyl)phenyl)-N-(pyrido[3,2-d]thiazole-2-yl)propionamide. (−)-3-[(1α,3α,4α)-3,4-difluorocyclopentyl]-2-(4-(methylsulfonyl)phenyl)-N-(3-methylthiadiazole-5-yl)propionamide may also be named as -(R)-3-[(1α,3α,4α)-3,4-difluorocyclopentyl]-2-(4-(methylsulfonyl)phenyl)-N-(3-methylthiadiazole-5-yl)propionamide or (R)-3-((1r,3R,4S)-3,4-difluorocyclopentyl)-2-(4-(methylsulfonyl)phenyl)-N-(3-methylthiadiazole-5-yl)propionamide.

The pharmaceutically acceptable salt may be any salt formed with an inorganic or organic acid, such as hydrochloric acid, hydrobromic acid, nitric acid, sulfuric acid, phosphoric acid, citric acid, formic acid, maleic acid, acetic acid, succinic acid and tartaric acid.

The compounds represented by the general formula (1) can be produced, for example, by the following production step using the compound of the general formula (3) as an intermediate.

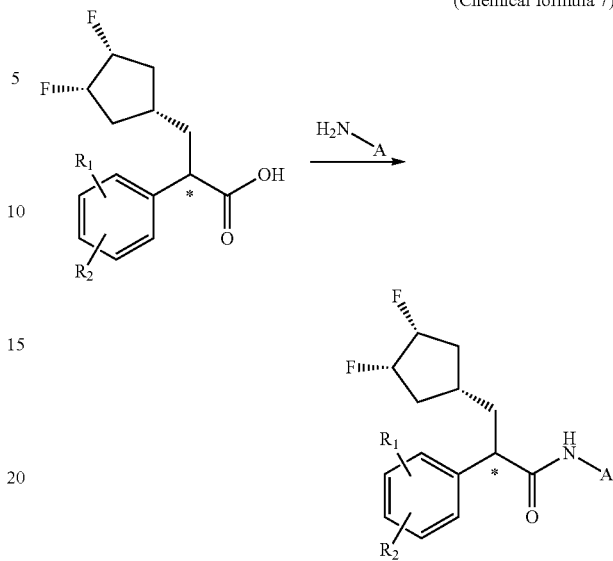

(Chemical formula 7)

(wherein *, $R^1$, $R^2$ and A are as described above.)

In this step, the compound of the general formula (3) is reacted with a heteroarylamine in the presence of suitable reagents to form the compound of the general formula (1).

The reaction can be carried out using a common condensation agent or using any of the following techniques: active ester technique, mixed acid anhydride technique, acid halide technique and carbodiimide technique. The reagents for use in these reactions include thionyl chloride, oxalyl chloride, N,N'-dicyclohexylcarbodiimide, N,N'-diisopropylcarbodiimide, 1-methyl-2-bromopyridinium iodide, N,N'-carbonyldiimidazole, diphenylphosphoric acid chloride, diphenylphosphoryl azide, N,N-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazo-1-yl-oxy-tris(dimethylamino)phosphonium hexafluorophosphate and N-bromosuccinimide/triphenylphosphine. In this step, a base or a condensation aid (condensation additive) may be used along with these reagents. The base may be any base that is not involved in the reaction. For example, the reaction may be carried out in the presence of an alkali metal alkoxide, such as sodium methoxide and sodium ethoxide, an alkali metal hydride, such as sodium hydride and potassium hydride, an alkali metal organic base, such as n-butyllithium, lithium bis(trimethylsilyl)amide, sodium bis(trimethylsilyl)amide and potassium bis(trimethylsilyl)amide, a tertiary organic base, such as triethylamine, diisopropylethylamine, pyridine, N-methylmorpholine, imidazole, N-methylpyrrolidine, N-methylpiperidine, 1,5-diazabicyclo[4.3.0]nona-5-ene and 1,8-diazabicyclo[5.4.0]unde-7-cene, or an inorganic base, such as potassium carbonate and sodium bicarbonate. The condensation aid may be N-hydroxybenzotriazole hydrate, N-hydroxysuccinimide, N-hydroxy-5-norbornene-2,3-dicarboxyimide, 3-hydroxy-3,4-dihydro-4-oxo-1,2,3-benzotriazole or pentafluorophenol. The reaction solvent may be any solvent that is not involved in the reaction. Preferred examples include hydrocarbon solvents, such as pentane, hexane, cyclohexane, benzene, toluene and xylene, halogenated hydrocarbon solvents, such as dichloromethane, 1,2-dichloroethane, chloroform and carbon tetrachloride, ether solvents, such as diethyl ether, tetrahydrofuran and 1,4-dioxane, and aprotic polar solvents, such as acetonitrile, propionitrile, nitromethane, nitroethane, N,N-dimethylformamide, N-methylpiperidone, sulfolane and dimethylsulfoxide. The reaction generally proceeds smoothly at −78 to 200° C.

In one aspect, the present invention concerns pharmaceuticals containing as an active ingredient any of the compounds represented by the general formula (1) or a pharmaceutically acceptable salt. The pharmaceuticals of the present invention are effective GK activators or hypoglycemic agents and are therefore useful in the treatment or prevention of type I diabetes, type II diabetes, hyperlipemia (hyper-LDL cholesterolemia, hypertriglyceridemia and hypo-HDL cholesterolemia), obesity, insulin resistance, abnormal glucose tolerance, metabolic syndrome and other disorders.

The pharmaceutical composition of the present invention may be orally administered, or it may be parenterally administered via intrarectal, subcutaneous, intravenous, intramuscular, or percutaneous route.

The compounds of the present invention or pharmaceutically acceptable salt may be provided in the form of a solid composition, a liquid composition or any other form suitable for use as pharmaceuticals. The pharmaceuticals of the present invention may be formulated with pharmaceutically acceptable carriers. Specifically, commonly used excipients, fillers, binders, disintegrating agents, coating agents, sugar-coating agents, pH adjusters, solubilizers, or aqueous or non-aqueous solvents are added and tablets, pills, capsules, granules, powders, powdered drugs, solutions, emulsions, suspensions or injections are formulated by commonly used drug preparation techniques.

While the dose of the compound of the present invention or pharmaceutically acceptable salt may vary depending on the type of disorder, symptoms, body weight, age and sex of the subject, as well as on the route of administration, the dose for oral administration to an adult is preferably in the range of approximately 0.01 to approximately 1000 mg/kg/day and, more preferably, in the range of approximately 0.5 to approximately 200 mg/kg/day. This amount is administered daily in a single or multiple doses.

When necessary, the compounds of the present invention or pharmaceutically acceptable salts thereof may be used in combination with one or more compounds other than GK activators. For example, they may be used in combination with one or more antidiabetic agents, antihyperglycemic agents or antiobesity agents containing sulfonylureas, biguanides, glucagon antagonists, α-glucosidase inhibitors, insulin secretion enhancers or insulin sensitizers.

Examples of the sulfonylurea include glyburide, glimepiride, glipyride, glipizide, chlorpropamide, gliclazide, glisoxepide, acetohexamide, glibornuride, tolbutamide, tolazamide, carbutamide, gliquidone, glyhexamide, phenbutamide and tolcyclamide. Examples of the biguanide include metformin, phenformin and buformin. Examples of the glucagon antagonist include peptide or non-peptide glucagon antagonists. Examples of the α-glucosidase inhibitor include acarbose, voglibose and miglitol. Examples of the insulin sensitizer include troglitazone, rosiglitazone, pioglitazone and ciglitazone. Examples of the antiobesity agent include sibutramine and orlistat. The compounds of the present invention or pharmaceutically acceptable salts thereof and other antidiabetic agents, antyhyperglycemic agents or antiobesity agents may be administered either simultaneously, sequentially or separately.

EXAMPLE 1

(±)-3-[(1α,3α,4α)-3,4-difluorocyclopentyl]-2-(4-(methylsulfonyl)phenyl)propionic acid (Chemical formula 8)

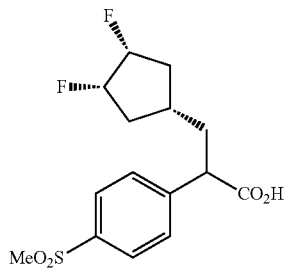

To a tetrahydrofuran solution (20 mL) of lithium diisopropylamide (10.2 mmol) containing N,N-dimethylpropyleneurea (3.92 mL), a solution of 4-methylsulfonylphenyl acetic acid (1.04 g) in tetrahydrofuran (7 mL) was added dropwise at −78° C. The mixture was stirred for 2 hours at −45 to −30° C. Subsequently, (1α,3α,4α)-3,4-difluorocyclopentylmethyl iodide (1.20 g) was added dropwise at −78° C. and the mixture was allowed to gradually warm to room temperature under stirring. Water (15 mL) was then added and tetrahydrofuran was evaporated under reduced pressure. To the resulting residue, 6 mol/L hydrochloric acid was added to a pH of 2. The mixture was then extracted with ethyl acetate and the organic layer was dried over anhydrous sodium sulfate, filtered and concentrated. Purification of the resulting residue by silica gel column chromatography afforded (±)-3-[(1α,3α,4α)-3,4-difluorocyclopentyl]-2-(4-(methylsulfonyl)phenyl)propionic acid (956 mg).

MS (CI$^+$) m/z: 333 (MH$^+$).
HRMS (CI$^+$) for $C_{15}H_{19}F_2O_4S$(MH$^+$): calcd, 333.0972. found, 333.0997.

EXAMPLE 2

(4R)-4-benzyl-3-[3-[(1α,3α,4α)-3,4-difluorocyclopentyl]-2-(4-(methylsulfonyl)phenyl)propanoyl]oxazolidine-2-one (Chemical formula 9)

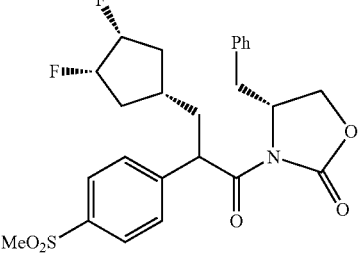

Triethylamine (975 mL) was added to a solution of (±)-3-[(1α,3α,4α)-3,4-difluorocyclopentyl]-2-(4-(methylsulfonyl)phenyl)propionic acid (931 mg) in tetrahydrofuran (12 mL). While the mixture was cooled in a salt-ice bath, pivaloyl chloride (362 mL) was added dropwise and the mixture was stirred for 1 hour. Subsequently, (R)-4-benzyloxazolidinone (494 mg) and lithium chloride (130 mg) were added and the mixture was further stirred at room temperature for 4 hours. The insoluble material was removed by filtration and the filtrate was concentrated. The resulting residue was dissolved in ethyl acetate. The solution was washed sequentially with a saturated aqueous sodium bicarbonate solution and a saturated sodium chloride solution, dried over anhydrous sodium sulfate, filtered and concentrated. Purification of the resulting residue by silica gel column chromatography (Si60NS, Kanto Chemical, Eluant:toluene:ethyl acetate=3:1) afforded a more polar isomer A (521 mg) and a less polar isomer B (433 mg) of (4R)-4-benzyl-3-[3-[(1α,3α,4α)-3,4-difluorocyclopentyl]-2-(4-(methylsulfonyl)phenyl)propanoyl]oxazolidine-2-one, the isomers A and B eluting in late fractions and early fractions, respectively.

Isomer A:
MS (EI) m/z: 491 (M$^+$).
HRMS (EI) for $C_{25}H_{27}F_2NO_5S$ (M$^+$): calcd, 491.1578. found, 491.1557.

Isomer B:
MS (EI) m/z: 491 (M$^+$).
HRMS (EI) for $C_{25}H_{27}F_2NO_5S$ (M$^+$): calcd, 491.1578. found, 491.1578.

EXAMPLE 3

(−)-3-[(1α,3α,4α)-3,4-difluorocyclopentyl]-2-(4-(methylsulfonyl)phenyl)propionic acid

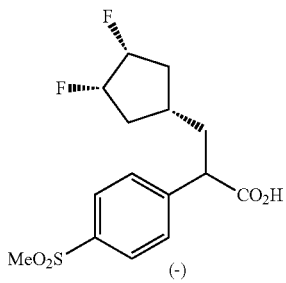

(Chemical formula 10)

To a tetrahydrofuran solution (5 mL) of isomer A of (4R)-4-benzyl-3-[3-[(1α,3α,4αα)-3,4-difluorocyclopentyl]-2-(4-(methylsulfonyl)phenyl)propanoyl]oxazolidine-2-one (250 mg), an aqueous solution (1.3 mL) of lithium hydroxide (24.0 mg) containing 30% hydrogen peroxide solution (206 μL) was added under cooling with ice. The mixture was stirred for 1 hour. Subsequently, a 1 mol/L aqueous sodium sulfite solution and a saturated sodium bicarbonate solution were added and the mixture was washed with ethyl acetate. 1 mol/L hydrochloric acid was added to the aqueous layer to pH 2 and the aqueous layer was extracted with ethyl acetate. The organic layer was washed with saturated sodium chloride solution, dried over anhydrous sodium sulfate, filtered and concentrated. The resulting residue was washed with diethyl ether to afford (−)-3-[(1α,3α,4α)-3,4-difluorocyclopentyl]-2-(4-(methylsulfonyl)phenyl)propionic acid (159 mg).

$^1$H NMR (CDCl$_3$) δ 1.62-2.33 (m, 7H), 3.06 (s, 1H), 3.71 (t, J=7.9 Hz, 1H), 4.71-4.93 (m, 2H), 7.53 (d, J=8.6 Hz, 2H), 7.93 (d, J=8.6 Hz, 2H).
MS (CI$^+$) m/z: 333 (MH$^+$).
HRMS (CI$^+$) for $C_{15}H_{19}F_2O_4S$ (MH$^+$): calcd, 333.0972. found, 333.0974.

EXAMPLE 4

(−)-3-[(1α,3α,4α)-3,4-difluorocyclopentyl]-2-(4-(methylsulfonyl)phenyl)-N-(thiazole-2-yl)propionamide (Compound No. 1)

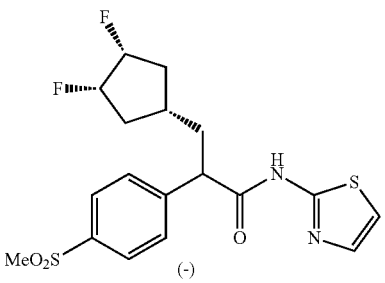

(Chemical formula 11)

N-bromosuccinimide (81.9 mg) was added to triphenylphosphine (120 mg) in dichloromethane (1.4 mL) under cooling with ice and the mixture was stirred for 30 min. Subsequently, (−)-3-[(1α,3α,4α)-3,4-difluorocyclopentyl]-2-(4-(methylsulfonyl)phenyl)propionic acid (90.6 mg) was added and the mixture was stirred for 40 min at room temperature. This was followed by the addition of 2-aminothiazole (67.8 mg) and stirring for additional 1.5 hours at room temperature. The reaction mixture was then diluted with ethyl acetate and washed sequentially with water, 1 mol/L hydrochloric acid, a 5% aqueous sodium bicarbonate solution and a saturated sodium chloride solution. The organic layer was then dried over anhydrous sodium sulfate, filtered and concentrated. Purification of the resulting residue by silica gel column chromatography afforded (−)-3-[(1α,3α,4α)-3,4-difluorocyclopentyl]-2-(4-(methylsulfonyl)phenyl)-N-(thiazole-2-yl)propionamide (106 mg).

$^1$H NMR (CDCl$_3$) δ 1.65-2.49 (m, 7H), 3.04 (s, 3H), 3.74 (t, J=7.3 Hz, 1H), 4.73-4.90 (m, 2H), 7.08 (d, J=3.7 Hz), 7.48-7.51 (m, 3H), 7.88 (d, J=8.6 Hz, 2H), 10.65 (brs, 1H).
MS (EI) m/z: 414 (M$^+$).
HRMS (EI) for $C_{25}H_{27}F_2NO_5S$ (M$^+$): calcd, 414.0883. found, 414.0890.

EXAMPLE 5

Compounds No. 2 through No. 89 were prepared as in Example 4. The optical rotation of each compound shown in the following table was determined using chloroform as a solvent except for DMSO used for Compound No. 7,15, and for DMF used for compound No. 17, 32, 4445, 47, 48, 49, 50, 54, 55, 56, 57, 58, 72, 73, 74, 75, 78.

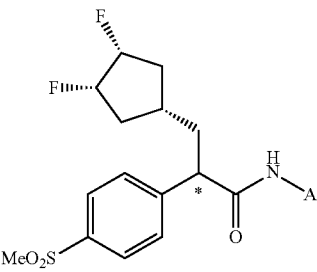

(Chemical formula 12)

(The carbon atom denoted by * is in the R-configuration)

TABLE 1

| Compound No. | Structure (A) | 1H NMR (400 MHz) | MS (m/z) | Optical rotation |
|---|---|---|---|---|
| 2 | (2-fluoro-5-methylthiazole) | (CDCl3) δ 1.67-1.85 (m, 3H), 2.01-2.18 (m, 3H), 2.37-2.44 (m, 1H), 3.06 (s, 3H), 3.65 (t, J = 7.7 Hz, 1H), 4.73-4.92 (m, 2H), 7.02 (d, J = 2.4 Hz, 1H), 7.51 (d, J = 8.6 Hz, 2H), 7.92 (d, J = 8.6 Hz, 2H), 9.42 (br, 1H). | (ESI+) 433.1 (MH+) | (−) |
| 3 | (1-methyl-3-methylpyrazole) | (d6DMSO) δ 1.49-1.81 (m, 4H), 2.04-2.17 (m, 3H), 3.17 (s, 3H), 3.69 (s, 3H), 3.88-3.92 (m, 1H), 4.81-4.97 (m, 2H), 6.39 (d, J = 1.8 Hz, 1H), 7.50 (d, J = 1.8 Hz, 1H), 7.62 (d, J = 8.6 Hz, 2H), 7.87 (d, J = 8.6 Hz, 2H), 10.7 (s, 1H). | (ESI+) 412.2 (MH+) | (−) |
| 4 | (2-methylthiazolo[5,4-b]pyridine) | (CDCl3) δ 1.73-1.89 (m, 3H), 2.04-2.20 (m, 3H), 2.42-2.49 (m, 1H), 3.08 (s, 3H), 3.75 (t, J = 7.7 Hz, 1H), 4.75-4.91 (m, 2H), 7.39 (dd, J = 8.6, 4.9 Hz, 1H), 7.53 (d, J = 8.6 Hz, 2H), 7.94-7.97 (m, 3H), 8.51-8.52 (m, 1H) | (ESI+) 466.1 (MH+) | (−) |
| 5 | (3,5-dimethyl-1,2,4-thiadiazole) | (CDCl3) δ 1.63-1.84 (m, 3H), 2.05-2.17 (m, 3H), 2.40-2.51 (m, 1H), 2.51 (s, 3H), 3.09 (s, 3H), 3.79 (t, J = 7.6 Hz, 1H), 4.74-4.91 (m, 2H), 7.52 (d, J = 8.6 Hz, 2H), 7.95 (d, J = 8.6 Hz, 2H), 9.47 (br, 1H). | (ESI+) 430.1 (MH+) | (−) |
| 6 | (2-methylthiazol-4-yl)CH2CO2Et | (CDCl3) δ 1.26 (t, J = 7.0 Hz, 3H), 1.71-1.83 (m, 3H), 2.03-2.17 (m, 3H), 2.39-2.45 (m, 1H), 3.07 (s, 3H), 3.64-3.68 (m, 3H), 4.16 (q, J = 7.1 Hz, 2H), 4.74-4.90 (m, 2H), 6.80 (s, 1H), 7.52 (d, J = 8.6 Hz, 2H), 7.94 (d, J = 8.6 Hz, 2H). | (ESI+) 501.2 (MH+) | (−) |
| 7 | (2-methylthiazol-4-yl)CH2CO2H | (d6DMSO) δ 1.49-1.73 (m, 3H), 1.82-1.89 (m, 1H), 2.04-2.25 (m, 3H), 3.18 (s, 3H), 3.56 (s, 2H), 3.99 (t, J = 7.4 Hz, 1H), 4.81-4.97 (m, 2H), 6.94 (s, 1H), 7.63 (d, J = 8.6 Hz, 2H), 7.89 (d, J = 8.6 Hz, 2H), 12.4 (br, 1H), 12.5 (br, 1H). | (ESI+) 473.1 (MH+) | (−) |
| 8 | (2-methylthiazol-4-yl)CO2Et | (CDCl3) δ 1.38 (t, J = 7.0 Hz, 3H), 1.66-1.80 (m, 3H), 2.01-2.17 (m, 3H), 2.39-2.46 (m, 1H), 3.08 (s, 3H), 3.75 (t, J = 7.3 Hz, 1H), 4.38 (q, J = 7.1 Hz, 2H), 4.72-4.88 (m, 2H), 7.42 (d, J = 6.7 Hz, 2H), 7.84 (s, 1H), 7.90 (d, J = 6.7 Hz, 2H), 9.41 (br, 1H). | (ESI+) 487.2 (MH+) | (−) |

TABLE 2

| Compound No. | Structure (A) | 1H NMR (400 MHz) | MS (m/z) | Optical rotation |
|---|---|---|---|---|
| 9 | (2-methylthiazol-4-yl)CO2H | (CDCl3) δ 1.73-1.99 (m, 3H), 2.12-2.24 (m, 3H), 2.42-2.49 (m, 1H), 3.04 (s, 3H), 3.93 (t, J = 7.7 Hz, 1H), 4.76-4.93 (m, 2H), 7.67 (d, J = 8.6 Hz, 2H), 7.94 (d, J = 8.8 Hz, 2H), 8.02 (s, 1H), 12.6 (br, 1H), 15.5 (br, 1H). | (ESI+) 459.1 (MH+) | (+) |
| 10 | (2-methylthiazol-5-yl)CO2Et | (CDCl3) δ 1.37 (t, J = 7.3 Hz, 3H), 1.69-1.87 (m, 3H), 2.04-2.18 (m, 3H), 2.39-2.46 (m, 1H), 3.07 (s, 3H), 3.74 (t, J = 7.3 Hz, 1H), 4.36 (q, J = 7.1 Hz, 2H), 4.74-4.92 (m, 2H), 7.52 (d, J = 8.6 Hz, 2H), 7.92 (d, J = 8.6 Hz, 2H), 8.07 (s, 1H), 9.87 (br, 1H). | (ESI+) 487.2 (MH+) | (−) |
| 11 | (2-methylthiazol-5-yl)CO2H | (d6DMSO) δ 1.51-1.71 (m, 3H), 1.88-1.95 (m, 1H), 2.04-2.24 (m, 3H), 3.18 (s, 3H), 4.06 (t, J = 7.7 Hz, 1H), 4.79-4.98 (m, 2H), 7.64 (d, J = 8.6 Hz, 2H), 7.90 (d, J = 8.6 Hz, 2H), 8.03 (s, 1H), 12.8 (br, 1H), 13.1 (br, 1H). | (ESI+) 459.1 (MH+) | (−) |

TABLE 2-continued

| Compound No. | Structure (A) | 1H NMR (400 MHz) | MS (m/z) | Optical rotation |
|---|---|---|---|---|
| 12 | 6-methylpyridine-3-carboxylic acid ethyl ester group | (CDCl3) δ 1.39 (t, J = 7.0 Hz, 3H), 1.66-1.88 (m, 3H), 2.01-2.21 (m, 3H), 2.37-2.45 (m, 1H), 3.06 (s, 3H), 3.63 (t, J = 7.7 Hz, 1H), 4.39 (q, J = 7.1 Hz, 2H), 4.71-4.92 (m, 2H), 7.58 (d, J = 7.9 Hz, 2H), 7.95 (d, J = 8.6 Hz, 2H), 8.06 (br, 1H), 8.24 (d, J = 8.6 Hz, 1H), 8.30 (dd, J = 8.6, 2.2 Hz, 1H), 8.86 (d, J = 2.5 Hz, 1H). | (ESI+) 481.2 (MH+) | (−) |
| 13 | 2-methyl-5-methoxy-thiazolo[5,4-b]pyridine | (CDCl3) δ 1.65-1.88 (m, 3H), 2.01-2.18 (m, 3H), 2.39-2.46 (m, 1H), 3.08 (s, 3H), 3.67 (t, J = 7.6 Hz, 1H), 4.01 (s, 3H), 4.73-4.91 (m, 2H), 6.83 (d, J = 8.6 Hz, 1H), 7.43 (d, J = 7.3 Hz, 2H), 7.84 (d, J = 8.6 Hz, 1H), 7.91 (d, J = 8.6 Hz, 2H), 9.11 (br, 1H). | (ESI+) 496.2 (MH+) | (−) |
| 14 | 3-methyl-1-(2-hydroxyethyl)pyrazole | (d6DMSO) δ 1.49-1.80 (m, 4H), 2.04-2.20 (m, 3H), 3.17 (s, 3H), 3.65 (dd, J = 11, 5.5 Hz, 2H), 3.88-3.92 (m, 1H), 3.98 (t, J = 5.5 Hz, 2H), 4.79-5.00 (m, 2H), 4.80 (t, J = 5.2 Hz, 1H), 6.40 (d, J = 1.8 Hz, 1H), 7.52 (d, J = 2.4 Hz, 1H), 7.62 (d, J = 8.6 Hz, 2H), 7.87 (d, J = 8.6 Hz, 2H), 10.8 (s, 1H). | (ESI+) 442.2 (MH+) | (−) |

TABLE 3

| No. | structure (A) | 1H NMR (400 MHz) | MS (m/z) | Optical rotation |
|---|---|---|---|---|
| 15 | 2-methyl-5-cyanothiazole | (CDCl3) δ 1.45-1.72 (m, 3H), 1.90-1.98 (m, 1H), 2.02-2.24 (m, 3H), 3.19 (s, 3H), 4.07 (t, J = 7.9 Hz, 1H), 4.77-5.00 (m, 2H), 7.64 (d, J = 8.6 Hz, 2H), 7.91 (d, J = 8.6 Hz, 2H), 8.12 (s, 0.3H), 8.37 (s, 0.7H), 13.3 (s, 1H). | (Cl) 440 (MH+) | (−) (DMSO) |
| 16 | 2,4-dimethylthiazole | (CDCl3) δ 1.56-1.87 (m, 4H), 1.98-2.20 (m, 3H), 2.32 (s, 1H), 2.38-2.45 (m, 1H), 3.07 (m, 3H), 3.63 (t, J = 7.6 Hz, 1H), 4.71-4.92 (m, 2H), 6.56 (s, 1H), 7.45 (d, J = 8.6 Hz, 2H), 7.90 (d, J = 8.6 Hz, 2H), 9.18 (br, 1H). | (ESI+) 429.2 (MH+) | (−) |
| 17 | 3-methyl-1-ethyl-pyrazole | (d6DMSO) δ 1.30 (t, J = 7.3 Hz, 3H), 1.45-1.65 (m, 2H), 1.66-1.80 (m, 2H), 2.20-2.04 (m, 3H), 3.17 (s, 3H), 3.90 (dd, J = 8.6, 6.1 Hz, 1H), 3.98 (q, J = 7.1 Hz, 2H), 4.79-5.00 (m, 2H), 6.39 (d, J = 2.4 Hz, 1H), 7.55 (d, J = 2.4 Hz, 1H), 7.62 (d, J = 8.6 Hz, 2H), 7.87 (d, J = 8.6 Hz, 2H), 10.8 (s, 1H). | (ESI+) 426.2 (MH+) | (+) (DMF) |
| 18 | 2-methyl-4-phenylthiazole | (d6DMSO) δ 1.45-1.78 (m, 2H), 1.71 (dt, J = 7.3, 7.9 Hz, 1H), 1.89 (ddd, J = 6.1, 6.9, 14.1 Hz, 1H), 2.02-2.28 (m, 2H), 2.23 (dt, J = 7.3, 7.9 Hz, 1H), 3.31, (s, 3H), 4.07 (t, J = 7.3 Hz, 1H), 4.77-5.02 (m, 2H), 7.30 (t, J = 7.6 Hz, 1H), 7.41 (t, J = 7.6 Hz, 2H), 7.62 (s, 1H), 7.66 (d, J = 7.6 Hz, 2H), 7.86 (d, J = 8.6 Hz, 2H), 7.90 (d, J = 8.6 Hz, 2H), 12.6 (s, 1H). | (ESI+) 491.2 (MH+) | (+) |
| 19 | 2-methyl-5-methyl-4,5,6,7-tetrahydrothiazolo[5,4-c]pyridine | (CDCl3) δ 1.56-1.86 (m, 3H), 1.98-2.18 (m, 3H), 2.37-2.44 (m, 1H), 2.49 (s, 3H), 2.69-2.82 (m, 4H), 3.07 (s, 3H), 3.58 (s, 2H), 3.63 (t, J = 7.4 Hz, 1H), 4.70-4.92 (m, 2H), 7.47 (d, J = 8.6 Hz, 2H), 7.90 (d, J = 8.6 Hz, 2H), 9.16 (s, 1H). | (ESI+) 484.2 (MH+) | (−) |

TABLE 4

| No. | structure (A) | 1H NMR (400 MHz) | MS (m/z) | Optical rotation |
|---|---|---|---|---|
| 20 | 2,5-dimethylthiazole | (CDCl3) δ 1.54-1.88 (m, 3H), 2.00-2.20 (m, 3H), 2.40-2.47 (m, 4H), 3.03 (s, 3H), 3.71 (t, J = 7.6 Hz, 1H), 4.93-4.72 (m, 2H), 6.39 (d, J = 2.4 Hz, 1H), 7.12 (d, J = 1.2 Hz, 1H), 7.48 (d, J = 8.6 Hz, 2H), 7.87 (d, J = 8.6 Hz, 2H), 10.89 (s, 1H). | (ESI+) 429.2 (MH+) | (−) |

TABLE 4-continued

| No. | structure (A) | 1H NMR (400 MHz) | MS (m/z) | Optical rotation |
|---|---|---|---|---|
| 21 | 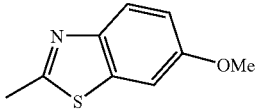 | (CHCl3) δ 1.63-1.82 (m, 3H), 1.96-2.17 (m, 3H), 2.34-2.41 (m, 1H), 3.06 (s, 3H), 3.61 (t, J = 7.6 Hz, 2H), 3.89 (s, 3H), 4.71-4.91 (m, 2H), 7.08 (dd, J = 2.4, 9.2 Hz, 1H), 7.23 (d, J = 8.6 Hz, 1H), 7.32 (d, J = 2.4 Hz, 1H), 7.65 (d, J = 9.2 Hz, 1H), 7.81 (d, J = 8.6 Hz, 2H), 9.84 (s, 1H). | (ESI+) 495.2 (MH+) | (−) |
| 22 | 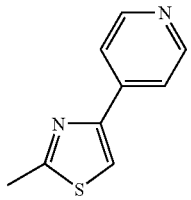 | (d6DMSO) δ 1.45-1.82 (m, 3H), 1.87-1.94 (m, 1H), 2.01-2.28 (m, 3H), 3.18 (s, 3H), 4.08 (t, J = 7.6 Hz, 1H), 4.78-5.01 (m, 2H), 7.67 (d, J = 8.6 Hz, 2H), 7.80 (dd, J = 1.8, 4.9 Hz, 2H), 7.91 (d, J = 8.6 Hz, 2H), 7.99 (s, 1H), 8.60 (dd, J = 1.8, 4.9 Hz, 2H), 12.7 (s, 1H). | (ESI+) 492.2 (MH+) | (+) |
| 23 | 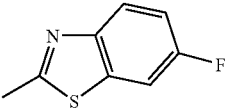 | (CHCl3) δ 1.61-1.85 (m, 3H), 2.01-2.18 (m, 3H), 2.38-2.45 (m, 1H), 3.07 (s, 3H), 3.66-3.73 (m, 1H), 4.75-4.89 (m, 2H), 7.16-7.22 (m, 1H), 7.41 (d, J = 8.6 Hz, 2H), 7.51-7.54 (m, 1H), 7.68 (q, J = 4.5 Hz, 1H), 7.87-7.91 (m, 2H), 9.47 (s, 1H). | (ESI+) 483.2 (MH+) | (−) |
| 24 | 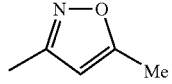 | (CDCl3) δ 1.66-1.86 (m, 3H), 2.02-2.22 (m, 3H), 2.33-2.40 (m, 1H), 2.46 (s, 3H), 3.03 (s, 3H), 3.79 (t, J = 7.6 Hz, 1H), 4.71-4.92 (m, 2H), 6.77 (s, 1H), 7.61 (d, J = 8.6 Hz, 2H), 7.90 (d, J = 8.6 Hz, 2H), 9.96 (s, 1H). | (ESI+) 413.2 (MH+) | (−) |
| 25 | 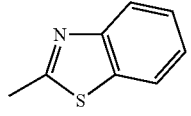 | (d6DMSO) δ 1.47-1.76 (m, 3H), 1.88-1.98 (m, 1H), 2.03-2.28 (m, 3H), 3.18 (s, 3H), 4.09 (t, J = 7.6 Hz, 1H), 4.79-5.00 (m, 2H), 7.29 (t, J = 7.6 Hz, 1H), 7.42 (t, J = 7.6 Hz, 1H), 7.67 (d, J = 8.6 Hz, 2H), 7.72 (d, J = 7.9 Hz, 1H), 7.92 (d, J = 8.6 Hz, 2H), 7.96 (d, J = 7.9 Hz, 1H), 12.7 (s, 1H). | (ESI+) 465.2 (MH+) | (−) |
| 26 | 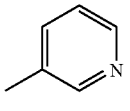 | (CDCl3) δ 1.75-1.89 (m, 3H), 1.95-2.03 (m, 1H), 2.06-2.21 (m, 2H), 2.33-2.42 (m, 1H), 3.08 (s, 3H), 3.68 (t, J = 7.6 Hz, 1H), 4.74-4.90 (m, 2H), 7.25-7.29 (m, 1H), 7.57 (d, J = 8.6 Hz, 2H), 7.88 (d, J = 8.6 Hz, 2H), 8.15-8.20 (m, 1H), 8.30-8.37 (m, 2H), 8.52 (d, J = 1.8 Hz, 1H). | (ESI+) 409.2 (MH+) | (−) |

TABLE 5

| No. | structure (A) | 1H NMR (400 MHz) | MS (m/z) | Optical rotation |
|---|---|---|---|---|
| 27 | 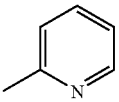 | (CDCl3) δ 1.66-1.90 (m, 3H), 1.99-2.06 (m, 1H), 2.09-2.22 (m, 2H), 2.38-2.45 (m, 1H), 3.05 (s, 3H), 3.61 (t, J = 7.3 Hz, 1H), 4.72-4.93 (m, 2H), 7.06 (dd, J = 6.7, 4.9 Hz, 1H), 7.57 (d, J = 7.9 Hz, 2H), 7.71 (td, J =7.9, 1.8 Hz, 2H), 7.93 (d, J = 7.9 Hz, 2H), 8.02 (s, 1H), 8.17 (d, J = 8.6 Hz, 1H), 8.24 (dd, J = 1.2, 4.9 Hz, 1H). | (ESI+) 409.2 (MH+) | (−) |
| 28 | 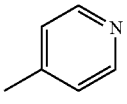 | (CDCl3) δ 1.70-1.91 (m, 3H), 1.96-2.03 (m, 1H), 2.07-2.21 (m, 2H), 2.33-2.42 (m, 1H), 3.07 (s, 3H), 3.64 (t, J = 7.6 Hz, 1H), 4.72-4.93 (m, 2H), 7.47-7.48 (m, 2H), 7.55 (d, J = 8.6 Hz, 2H), 7.89 (d, J = 8.6 Hz, 2H), 8.07 (s, 1H), 8.45-8.47(m, 2H). | (ESI+) 409.2 (MH+) | (−) |
| 29 | 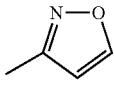 | (CDCl3) δ 1.68-1.86 (m, 3H), 2.02-2.24 (m, 3H), 2.35-2.43 (m, 1H), 3.04 (s, 3H), 3.78 (t, J = 7.3 Hz, 1H), 4.72-4.92 (m, 2H), 7.13 (d, J = 1.8 Hz, 2H), 7.60 (d, J = 8.6 Hz, 2H), 7.91 (d, J = 8.6 Hz, 2H), 8.36 (d, J = 1.8 Hz, 2H), 9.73 (s, 1H). | (ESI+) 399.2 (MH+) | (−) |
| 30 | 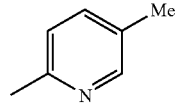 | (CDCl3) δ 1.64-1.78 (m, 3H), 1.98-2.05 (m, 1H), 2.08-2.22 (m, 2H), 2.28 (s, 3H), 2.37-2.44 (m, 1H), 3.05 (s, 3H), 3.59 (t, J = 7.6 Hz, 1H), 4.71-4.92 (m, 2H), 7.52 (dd, J = 8.6, 2.4 Hz, 1H), 7.56 (d, J = 8.6 Hz, 2H), 7.92 (d, J = 8.6 Hz, 2H), 8.02-8.07 (m, 3H). | (ESI+) 423.2 (MH+) | (−) |

TABLE 5-continued

| No. | structure (A) | 1H NMR (400 MHz) | MS (m/z) | Optical rotation |
|---|---|---|---|---|
| 31 | | (d6DMSO) δ 1.47-1.73 (m, 3H), 1.87-1.94 (m, 1H), 2.02-2.22 (m, 3H), 2.04-2.26 (m, 9H), 2.45-2.50 (m, 2H), 3.02 (s, 3H), 3.18 (s, 3H), 3.64 (t, J = 6.7 Hz, 2H), 4.05 (t, J = 7.6 Hz, 1H), 4.79-5.00 (m, 2H), 6.77 (s, 1H), 6.72 (d, J = 9.2 Hz, 2H), 7.66 (d, J = 8.6 Hz, 2H), 7.80 (d, J = 9.2 Hz, 2H), 7.91 (d, J = 8.6 Hz, 2H), 12.4 (s, 1H). | (ESI+) 566.2 (MH+) | (−) |
| 32 | | (CDCl3) δ 1.67-1.92 (m, 3H), 1.96-2.05 (m, 1H), 2.06-2.23 (m, 2H), 2.39-2.48 (m, 1H), 3.04 (s, 3H), 4.71-4.80 (m, 1H), 4.84-4.93 (m, 1H), 7.05 (t, J = 4.9 Hz, 1H), 7.62 (d, J = 8.6 Hz, 2H), 7.90 (d, J = 8.6 Hz, 2H), 8.35 (br, 1H), 8.61 (d, J = 4.9 Hz, 2H). | (ESI+) 410.2 (MH+) | (−) (DMF) |

TABLE 6

| No. | structure (A) | 1H NMR (400 MHz) | MS (m/z) | Optical rotation |
|---|---|---|---|---|
| 33 | | (d6DMSO) δ 1.44-1.79 (m, 3H), 1.79-1.93 (m, 1H), 1.98-2.25 (m, 3H), 3.20 (s, 3H), 4.12 (t, J = 7.3 Hz, 1H), 4.75-5.02 (m, 2H), 7.67 (d, J = 8.6 Hz, 2H), 7.91 (d, J = 8.6 Hz, 2H), 8.35 (d, J = 2.4 Hz, 1H), 8.38 (dd, J = 1.2, 2.4 Hz, 1H), 9.3 (d, J = 1.2 Hz, 1H), 11.2 (s, 1H). | (ESI+) 410.2 (MH+) | (−) |
| 34 | | (d6DMSO) δ 1.45-1.79 (m, 3H), 1.80-1.91 (m, 1H), 2.00-2.24 (m, 3H), 3.18 (s, 3H), 4.13 (t, J = 7.3 Hz, 1H), 4.78-5.01 (m, 2H), 7.66 (d, J = 8.6 Hz, 2H), 7.89 (d, J = 8.6 Hz, 2H), 8.18 (d, J = 8.6 Hz, 1H), 8.23 (dd, J = 1.8, 8.6 Hz, 1H), 8.77 (t, J = 1.2 Hz, 1H), 11.4 (s, 1H). | (ESI+) 434.2 (MH+) | (−) |
| 35 | | (d6DMSO) δ 1.45-1.77 (m, 3H), 1.77-1.89 (m, 1H), 1.99-2.25 (m, 3H), 3.18 (s, 3H), 4.09 (t, J = 7.9 Hz, 1H), 4.78-5.01 (m, 2H), 7.65 (d, J = 8.6 Hz, 2H), 7.87 dd, J = 2.4, 9.2 Hz, 1H), 7.89 (d, J = 8.6 Hz, 2H), 8.08 (d, J = 9.2 Hz, 1H), 8.35 (d, J = 2.4 Hz, 1H), 11.0 (s, 1H). | (ESI+) 443.2 (MH+) | (−) |
| 36 | | (d6DMSO) δ 1.42-1.77 (m, 3H), 1.77-1.88 (m, 1H), 2.00-2.24 (m, 3H), 3.18 (s, 3H), 4.08 (t, J = 7.9 Hz, 1H), 4.78-5.04 (m, 2H), 7.68 (d, J = 8.6 Hz, 2H), 7.71 (dt, J = 3.1, 9.2 Hz, 1H), 7.88 (d, J = 8.6 Hz, 2H), 8.09 (dd, J = 3.1, 9.2 Hz, 1H), 8.31 (d, J = 3.1 Hz, 1H), 11.0 (s, 1H). | (ESI+) 427.2 (MH+) | (−) |
| 37 | | (d6DMSO) δ 1.43-1.92 (m, 4H), 2.02-2.29 (m, 3H), 3.17 (s, 3H), 4.08 (t, J = 7.3 Hz, 1H), 4.74-5.02 (m, 2H), 7.52 (dt, J = 1.2, 7.3 Hz, 1H), 7.69 (dt, J = 1.2, 7.3 Hz, 1H), 7.70 (d, J = 8.6 Hz, 2H), 7.86 (d, J = 7.9 Hz, 1H), 7.89 (d, J = 8.6 Hz, 2H), 8.03 (d, J = 7.9 Hz, 1H), 8.45 (s, 1H), 9.13 (s, 1H), 11.0 (s, 1H). | (ESI+) 459.2 (MH+) | (−) |
| 38 | | (d6DMSO) δ 1.44-1.86 (m, 4H), 2.00-2.22 (m, 3H), 2.27 (s, 3H), 3.17 (s, 3H), 4.09 (t, J = 7.3 Hz, 1H), 4.74-5.02 (m, 2H), 6.93 (d, J = 4.9 Hz, 1H), 7.66 (d, J = 8.6 Hz, 2H), 7.88 (d, J = 8.6 Hz, 2H), 7.89 (d, J = 4.9 Hz, 1H), 8.14 (d, J = 5.5 Hz, 1H), 10.8 (s, 1H). | (ESI+) 423.2 (MH+) | (−) |

TABLE 7

| No. | structure (A) | 1H NMR (400 MHz) | MS (m/z) | Optical rotation |
|---|---|---|---|---|
| 39 | | (d6DMSO) δ 1.45-1.87 (m, 3H), 1.88-1.95 (m, 1H), 2.06-2.29 (m, 3H), 3.19 (s, 3H), 4.17 (t, J = 7.3 Hz, 1H), 4.76-5.02 (m, 2H), 7.71 (d, J = 7.9 Hz, 2H), 7.72 (dd, J = 1.8, 8.6 Hz, 1H), 7.80 (ddd, J = 1.2, 1.8, 7.3 Hz, 1H), 7.87 (dd, J = 1.2, 7.3 Hz, 1H), 7.91 (d, J = 7.9 Hz, 2H), 8.03 (dd, J = 1.2, 7.3 Hz, 1H), 9.61 (s, 1H), 11.5 (s, 1H). | (ESI+) 460.2 (MH+) | (+) |

TABLE 7-continued

| No. | structure (A) | 1H NMR (400 MHz) | MS (m/z) | Optical rotation |
|---|---|---|---|---|
| 40 | 2-methylquinoline | (d6DMSO) δ 1.46-1.92 (m, 4H), 2.01-2.26 (m, 3H), 3.18 (s, 3H), 4.17 (t, J = 7.3 Hz, 1H), 4.75-5.03 (m, 2H), 7.48 (m, 1H), 7.70 (m, 1H), 7.71 (d, J = 8.6 Hz, 2H), 7.79 (d, J = 1.8, 8.6 Hz, 1H), 7.80 (d, J = 8.6 Hz, 1H), 7.89 (m, 1H), 7.90 (d, J = 8.6 Hz, 2H), 8.26 (d, J = 9.2 Hz, 1H), 8.33 (d, J = 9.2 Hz, 1H), 11.2 (s, 1H). | (ESI+) 459.2 (MH+) | (+) |
| 41 | 6-methyl-2-(trifluoromethyl)pyridine | (d6DMSO) δ 1.43-1.77 (m, 3H), 1.79-1.91 (m, 1H), 1.99-2.25 (m, 3H), 3.18 (s, 3H), 4.15 (t, J = 7.3 Hz, 1H), 4.75-5.03 (m, 2H), 7.58 (d, J = 7.3 Hz, 1H), 7.66 (d, J = 8.6 Hz, 2H), 7.89 (d, J = 8.6 Hz, 2H), 7.79 (d, J = 1.8, 8.6 Hz, 1H), 8.05 (t, J = 7.9 Hz, 1H), 8.34 (d, J = 8.6 Hz, 1H), 11.3 (s, 1H). | (ESI+) 477.2 (MH+) | (−) |
| 42 | 3,5-difluoro-2-methylpyridine | (d6DMSO) δ 1.50-1.68 (m, 2H), 1.72-1.86 (m, 2H), 2.07-2.21 (m, 3H), 3.20 (s, 3H), 3.95 (t, J = 7.3 Hz, 1H), 4.80-5.02 (m, 2H), 7.64 (d, J = 8.6 Hz, 2H), 7.90 (d, J = 8.6 Hz, 2H), 7.99 (ddd, J = 9.8, 8.6, 2.4 Hz, 1H), 8.31 (d, J = 2.4 Hz, 1H), 10.6 (s, 1H). | (ESI+) 445.2 (MH+) | (−) |
| 43 | 1-cyclohexyl-3-methylpyrazole | (CDCl3) δ 1.15-1.43 (m, 4H), 1.55-1.76 (m, 4H), 1.83-1.91 (m, 3H), 1.95-2.20 (m, 5H), 2.38-2.45 (m, 1H), 3.05 (s, 3H), 3.54 (t, J = 7.7 Hz, 1H), 3.89 (tt, J = 1.6, 3.8 Hz, 1H), 4.71-4.91 (m, 2H), 6.62 (d, J = 2.4 Hz, 1H), 7.29 (1H, d, J = 2.4 Hz, 1H), 7.56 (dd, J = 8.6 Hz, 2H), 7.86 (s, 1H), 7.91 (d, J = 8.6 Hz, 2H). | (ESI+) 480.2 (MH+) | (−) |
| 44 | 1-cyclopentyl-3-methylpyrazole | (CDCl3) δ 1.66-2.02 (m, 10H), 2.05-2.22 (m, 4H), 2.37-2.45 (m, 1H), 3.05 (s, 3H), 3.53 (t, J = 7.6 Hz, 1H), 4.43-4.50 (m, 1H), 4.70-4.92 (m, 2H), 6.62 (d, J = 2.4 Hz, 1H), 7.30 (d, J = 2.4 Hz, 1H), 7.56 (dd, J = 8.6 Hz, 2H), 7.76 (s, 1H), 7.92 (d, J = 8.6 Hz, 2H). | (ESI+) 466.2 (MH+) | (+) (DMF) |

TABLE 8

| No. | structure (A) | 1H NMR (400 MHz) | MS (m/z) | Optical rotation |
|---|---|---|---|---|
| 45 | 1-(2-fluoroethyl)-3-methylpyrazole | (d6DMSO) δ 1.44-1.82 (m, 4H), 2.03-2.21 (m, 3H), 3.17 (s, 3H), 3.28-3.32 (m, 1H), 3.88-3.94 (m, 1H), 4.28 (dt, J = 27.7, 4.7 Hz, 2H), 4.68 (dt, J = 47.3, 4.7 Hz, 2H), 4.78-5.00 (m, 2H), 6.45 (d, J = 2.4 Hz, 1H), 7.60 (d, J = 2.4 Hz, 1H), 7.63 (d, J = 8.6 Hz, 2H), 7.87 (d, J = 8.6 Hz, 2H), 10.8 (s, 1H). | (ESI+) 444.2 (MH+) | (+) (DMF) |
| 46 | 2,5-dimethylpyrazine | (d6DMSO) δ 1.43-1.91 (m, 4H), 2.00-2.24 (m, 3H), 2.42 (s, 3H), 3.18 (s, 3H), 4.09 (t, J = 7.3 Hz, 1H), 4.77-5.01 (m, 2H), 7.67 (d, J = 8.6 Hz, 1H), 7.89 (d, J = 8.6 Hz, 1H), 8.27 (d, J =1.2 Hz, 1H), 9.16 (d, J = 1.2 Hz, 1H), 11.0 (s, 1H). | (ESI+) 423.2 (MH+) | (−) |
| 47 | N,N-diethyl-2-(3-methylpyrazol-1-yl)acetamide | (CDCl3) δ 1.12 (t, J = 7.0 Hz, 3H), 1.21 (t, J = 7.0 Hz, 3H), 1.63-1.90 (m, 3H), 1.94-2.01, (m, 1H), 2.07-2.20 (m, 2H), 2.37-2.44 (m, 1H), 3.05 (s, 3H), 3.30-3.41 (m, 4H), 3.54 (t, J = 7.6 Hz, 1H), 4.71-4.77 (m, 2H), 6.72 (d, J = 2.4 Hz, 1H), 7.37 (d, J = 2.4 Hz, 1H), 7.54 (d, J = 8.6 Hz, 2H), 7.75 (s, 1H), 7.91 (d, J = 8.6 Hz, 2H). | (ESI+) 511.2 (MH+) | (+) (DMF) |
| 48 | 2-isopropyl-5-methylpyrrole | (CDCl3) δ 1.43 (d, J = 6.7 Hz, 6H), 1.66-1.89 (m, 3H), 1.95-2.02 (m, 1H), 2.08-2.20 (m, 2H), 2.38-2.45 (m, 1H), 3.05 (s, 3H), 3.54 (t, J = 7.6 Hz, 1H), 4.27-4.34 (m, 1H), 4.71-4.92 (m, 2H), 6.62 (d, J = 2.4 Hz, 1H), 7.30 (d, J = 2.4 Hz, 1H), 7.56 (d, J = 8.6 Hz, 2H), 7.79 (s, 1H), 7.92 (d, J = 8.6 Hz, 2H). | (ESI+) 440.2 (MH+) | (+) (DMF) |
| 49 | 1-tert-butyl-3-methylpyrazole | (CDCl3) δ 1.50 (s, 9H), 1.66-1.90 (m, 3H), 1.95-2.02 (m, 1H), 2.09-2.21 (m, 1H), 3.05 (s, 3H), 3.54 (t, J = 7.6 Hz, 1H), 4.71-4.92 (m, 2H), 6.62 (d, J = 2.4 Hz, 1H), 7.39 (d, J = 2.4 Hz, 1H), 7.57 (d, J = 8.6 Hz, 2H), 7.79 (s, 1H), 7.92 (d, J = 8.6 Hz, 2H). | (ESI+) 454.2 (MH+) | (+) (DMF) |

TABLE 8-continued

| No. | structure (A) | 1H NMR (400 MHz) | MS (m/z) | Optical rotation |
|---|---|---|---|---|
| 50 | 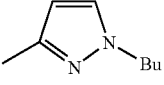 | (CDCl3) δ 0.91 (t, J = 7.3 Hz, 3H), 1.28 (q, J = 7.3 Hz, 2H), 1.66-1.87 (m, 2H), 1.96-2.20 (m, 3H), 2.38-2.45 (m, 1H), 3.05 (s, 3H), 3.54 (t, J = 7.6 Hz, 1H), 3.95 (t, J = 7.0 Hz, 2H), 4.71-4.91 (m, 2H), 6.62 (d, J = 2.4 Hz, 1H), 7.25 (d, J = 2.4 Hz, 1H), 7.56 (d, J = 8.6 Hz, 2H), 7.70 (s, 1H), 7.92 (d, J = 8.6 Hz, 2H). | (ESI+) 454.2 (MH+) | (+) (DMF) |

TABLE 9

| No. | structure (A) | 1H NMR (400 MHz) | MS (m/z) | Optical rotation |
|---|---|---|---|---|
| 51 | 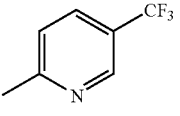 | (d6DMSO) δ 1.43-1.77 (m, 3H), 1.78-1.89 (m, 1H), 1.99-2.26 (m, 3H), 3.18 (s, 3H), 4.14 (t, J = 7.3 Hz, 1H), 4.76-5.02 (m, 2H), 7.66 (d, J = 8.6 Hz, 2H), 7.90 (d, J = 8.6 Hz, 2H), 8.16 (dd, J = 2.4, 8.4 Hz, 1H), 8.24 (d, J = 8.4 Hz, 1H), 8.70 (d, J = 2.4 Hz, 1H), 11.3 (s, 1H). | (ESI+) 477.1 (MH+) | (−) |
| 52 | 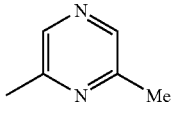 | (d6DMSO) δ 1.42-1.88 (m, 4H), 2.00-2.26 (m, 3H), 2.41 (s, 3H), 3.18 (s, 3H), 4.11 (t, J = 7.3 Hz, 1H), 4.76-5.02 (m, 2H), 7.66 (d, J = 8.6 Hz, 2H), 7.89 (d, J = 8.6 Hz, 2H), 8.25 (s, 1H), 9.11 (s, 1H), 11.1 (s, 1H). | (ESI+) 424.1 (MH+) | (−) |
| 53 | 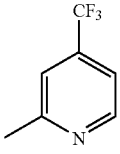 | (CDCl3) δ 1.74-1.88 (m, 3H), 2.01-2.08 (m, 1H), 2.10-2.23 (m, 2H), 2.42 (dt, J = 15.3, 7.9 Hz, 1H), 3.06 (s, 1H), 3.64 (t, J = 7.6 Hz, 1H), 4.72-4.94 (m, 2H), 7.28 (s, 1H), 7.59 (dt, J = 8.6, 1.8 Hz, 2H), 7.96 (dt, J = 8.6, 1.8 Hz, 2H), 8.07 (s, 1H), 8.40 (d, J = 4.9 Hz, 1H), 8.48 (s, 1H). | (ESI+) 477 (MH+) | (−) |
| 54 | 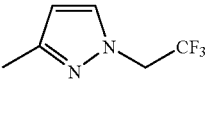 | (CDCl3) δ 1.65-1.89 (m, 3H), 1.97-2.05 (m, 1H), 2.09-2.20 (m, 2H), 2.36-2.44 (m, 1H), 3.06 (s, 3H), 3.56 (t, J = 7.6 Hz, 1H), 4.53 (q, J = 8.4 Hz, 2H), 4.71-4.91 (m, 2H), 6.81 (d, J = 2.4 Hz, 1H), 7.38 (d, J = 2.4 Hz, 1H), 7.56 (d, J = 8.6 Hz, 2H), 7.80 (s, 1H), 7.93 (d, J = 8.6 Hz, 2H). | (ESI+) 480.1 (MH+) | (+) (DMF) |
| 55 | 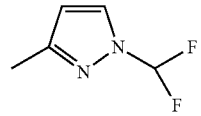 | (CDCl3) δ 1.66-1.89 (m, 3H), 1.98-2.20 (m, 3H), 2.37-2.44 (m, 1H), 3.06 (s, 3H), 3.59 (t, J = 7.6 Hz, 1H), 4.72-4.92 (m, 2H), 6.94 (d, J = 3.1 Hz, 1H), 6.97 (t, J = 61.1 Hz, 1H), 7.56 (d, J = 8.6 Hz, 1H), 7.69 (d, J = 3.1 Hz, 1H), 7.79 (s, 1H), 7.94 (d, J = 8.6 Hz, 2H). | (ESI+) 448.1 (MH+) | (+) (DMF) |
| 56 | 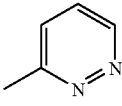 | (CDCl3) δ 1.71-1.91 (m, 3H), 2.03-2.25 (m, 3H), 2.34-2.41 (m, 1H), 3.01 (s, 3H), 4.67-4.91 (m, 3H), 7.60 (dd, J = 9.2, 4.9 Hz, 1H), 7.71 (d, J = 8.6 Hz, 2H), 7.86 (d, J = 8.6 Hz, 1H), 8.69 (dd, J = 9.2, 1.8 Hz, 1H), 9.01 (dd, J = 4.9, 1.8 Hz, 1H), 11.4 (s, 1H). | (ESI+) 410.1 (MH+) | (−) (DMF) |

TABLE 10

| No. | structure (A) | 1H NMR (400 MHz) | MS (m/z) | Optical rotation |
|---|---|---|---|---|
| 57 | 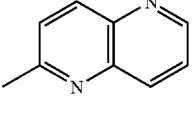 | (d6DMSO) δ 1.49-1.79 (m, 3H), 1.84-1.91 (m, 1H), 2.05-2.27 (m, 3H), 3.18 (s, 3H), 4.22-4.15 (m, 1H), 4.79-5.01 (m, 2H), 7.70-7.74 (m, 3H), 7.91 (d, J = 8.6 Hz, 2H), 8.18 (d, J = 8.6 Hz, 1H), 8.39 (d, J = 9.2 Hz, 1H), 8.49 (d, J = 9.2 Hz, 1H), 8.86 (q, J = 2.0 Hz, 1H), 11.3 (s, 2H). | (ESI+) 460.2 (MH+) | (+) (DMF) |
| 58 | 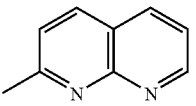 | (d6DMSO) δ 1.48-1.80 (m, 3H), 1.84-1.91 (m, 1H), 2.05-2.27 (m, 3H), 3.18 (s, 3H), 4.21-4.15 (m, 1H), 4.79-5.01 (m, 2H), 7.51 (dd, J = 8.6, 4.3 Hz, 1H), 7.71 (d, J = 7.9 Hz, 2H), 7.91 (d, J = 8.6 Hz, 2H), 8.37 (dd, J = 7.9, 1.8 Hz, 2H), 8.43 (d, J = 9.2 Hz, 1H), 8.98 (q, J = 4.3, 1.8 Hz, 1H), 11.5 (s, 1H). | (ESI+) 460.2 (MH+) | (+) (DMF) |

TABLE 10-continued

| No. | structure (A) | 1H NMR (400 MHz) | MS (m/z) | Optical rotation |
|---|---|---|---|---|
| 59 | (4-tert-butyl-2-methylthiazole) | (CDCl3) δ 1.26 (s, 9H), 1.65-1.91 (m, 3H), 1.97-2.22 (m, 3H), 2.38-2.48 (m, 1H), 3.06 (s, 3H), 3.64 (t, J = 7.3 Hz, 1H), 4.70-4.93 (m, 2H), 6.55 (s, 1H), 7.55 (d, J = 8.6 Hz, 2H), 7.94 (d, J = 8.6 Hz, 2H), 8.80 (br, 1H). | (ESI+) 471.2 (MH+) | (−) |
| 60 | (2-methylthiazolo[5,4-b]pyridine with OCH2CH2OMe) | (CDCl3) δ 1.65-1.88 (m, 3H), 2.01-2.17 (m, 3H), 2.38-2.47 (m, 1H), 3.08 (s, 3H), 3.46 (s, 3H), 3.68 (t, J = 7.6 Hz, 1H), 3.77-3.80 (m, 2H), 4.53-4.56 (m, 2H), 4.71-4.93 (m, 2H), 6.87 (d, J = 9.2 Hz, 1H), 7.46 (d, J = 8.6 Hz, 2H), 7.83 (d, J = 9.2 Hz, 1H), 7.91 (d, J = 8.6 Hz, 2H), 9.20 (s, 1H). | (ESI+) 540.1 (MH+) | (−) |
| 61 | (2-methyl-5-methylthiopyridine) | (CDCl3) δ 1.72-1.87 (m, 3H), 1.98-2.07 (m, 1H), 2.07-2.21 (m, 2H), 2.36-2.45 (m, 1H), 2.47 (s, 3H), 3.05 (s, 3H), 3.59 (t, J = 7.3 Hz, 1H), 4.71-4.93 (m, 2H), 7.57 (dt, J = 8.6, 1.8 Hz, 2H), 7.63 (dd, J = 8.6, 2.4 Hz, 1H), 7.89 (s, 1H), 7.94 (dt, J = 8.6, 1.8 Hz, 2H), 8.12 (d, J = 8.6 Hz, 1H), 8.16 (d, J = 2.4 Hz, 1H). | (ESI+) 455.1 (MH+) | (−) |
| 62 | (methyl 2-methylnicotinate) | (CDCl3) δ 1.68-1.86 (m, 2H), 1.87-2.04 (m, 2H), 2.11-2.25 (m, 2H), 2.44-2.52 (m, 1H), 3.04 (s, 3H), 3.94 (s, 3H), 4.02 (s, 1H), 4.71-4.93 (m, 2H), 7.08 (dd, J = 7.9, 4.9 Hz, 1H), 7.66 (dt, J = 8.9, 1.8 Hz, 2H), 7.91 (dt, J = 8.6, 1.8 Hz, 2H), 8.30 (dd, J = 7.6, 1.8 Hz, 1H), 8.61 (dd, J = 4.9, 1.8 Hz, 1H), 11.1 (s, 1H). | ESI+) 467.1 (MH+) | (+) |

TABLE 11

| No. | structure (A) | 1H NMR (400 MHz) | MS (m/z) | Optical rotation |
|---|---|---|---|---|
| 63 | (3,5-dimethylisoxazole) | (CDCl3) δ 1.66-1.85 (m, 3H), 1.98-2.06 (m, 1H), 2.08-2.18 (m, 2H), 2.26 (s, 3H), 2.33-2.42 (m, 1H), 3.08 (s, 3H), 3.69 (t, J = 7.6 Hz, 1H), 4.71-4.94 (m, 2H), 6.23 (s, 1H), 7.54 (d, J = 8.6 Hz, 2H), 7.92 (d, J = 8.6 Hz, 2H), 8.67 (s, 1H). | (ESI+) 413.1 (MH+) | (−) |
| 64 | (3-isopropyl-5-methylisoxazole) | (CDCl3) δ 1.26 (dd, J = 7.3, 1.8 Hz, 6H), 1.65-1.88 (m, 3H), 1.98-2.20 (m, 3H), 2.38 (dt, J = 13.4, 7.3 Hz, 1H), 2.95-3.05 (m, 1H), 3.08 (s, 3H), 3.68 (t, J = 7.3 Hz, 1H) 4.72-4.94 (m, 2H), 6.27 (s, 1H), 7.54 (dt, J = 8.6, 1.8 Hz, 2H), 7.92 (dt, J = 8.6, 1.8 Hz, 2H), 8.51 (s, 1H). | (ESI+) 441.2 (MH+) | (−) |
| 65 | (ethyl 2-methyloxazole-5-carboxylate) | (CDCl3) δ 1.37 (t, J = 7.3 Hz, 3H), 1.65-1.89 (m, 3H), 1.96-2.05 (m, 1H), 2.06-2.21 (m, 2H), 2.34-2.43 (m, 1H), 3.08 (s, 3H), 4.37 (q, J = 7.3 Hz, 2H), 4.71-4.93 (m, 2H), 7.57 (d, J = 7.9 Hz, 2H), 7.62 (s, 1H), 7.91 (dt, J = 8.6, 1.8 Hz, 2H), 8.85 (s, 1H). | (ESI+) 471.1 (MH+) | (−) |
| 66 | (2-methyl-5-methylsulfonylpyridine) | (CDCl3) δ 1.67-1.89 (m, 3H), 2.02-2.21 (m, 3H), 2.36-2.45 (m, 1H), 3.07 (s, 3H), 3.08 (s, 3H), 3.68 (t, J = 7.3 Hz, 1H), 4.72-4.93 (m, 2H), 7.58 (dt, J = 7.9, 1.8 Hz, 2H), 7.96 (dt, J = 7.9, 1.8 Hz, 2H), 8.18-8.22 (m, 2H), 8.39 (d, J = 9.2 Hz, 1H), 8.77 (d, J = 2.4 Hz, 1H). | (ESI+) 487.1 (MH+) | (−) |
| 67 | (3,5-dimethylisothiazole) | (CDCl3) δ 1.64-1.78 (m, 2H), 1.80-1.92 (m, 1H), 1.94-2.02 (m, 1H), 2.07-2.21 (m, 2H), 2.35 (s, 3H), 2.36-2.45 (m, 1H), 3.09 (s, 3H), 3.75 (dd, J = 7.9, 6.7 Hz, 1H), 4.71-4.93 (m, 2H), 6.60 (s, 1H), 7.52 (dt, J = 8.6, 1.8 Hz, 2H), 7.85 (dt, J = 8.6, 1.8 Hz, 2H), 9.32 (s, 1H). | (ESI+) 429.1 (MH+) | (−) |
| 68 | (5-chloro-2-methylthiazole) | (CDCl3) δ 1.64-1.88 (m, 3H), 2.00-2.21 (m, 3H), 2.37-2.46 (m, 1H), 3.07 (s, 3H), 3.70 (t, J = 7.3 Hz, 1H), 4.71-4.93 (m, 2H), 7.25 (s, 1H), 7.49-7.55 (m, 2H), 7.91-7.96 (m, 2H), 9.28 (s, 1H). | (ESI+) 449.0 (MH+) | (−) |

TABLE 12

| No. | structure (A) | 1H NMR (400 MHz) | MS (m/z) | Optical rotation |
|---|---|---|---|---|
| 69 | (2-methylthiazol-4-yl)-pyridin-3-yl | (CDCl3) δ 1.66-1.99 (m, 3H), 2.02-2.28 (m, 3H), 2.49-2.59 (m, 1H), 3.02 (s, 3H), 4.03 (t, J = 7.3 Hz, 1H), 4.69-4.95 (m, 2H), 7.32 (s, 1H), 7.47-7.53 (m, 1H), 7.60 (d, J = 8.6 Hz, 2H), 7.89 (d, J = 8.6 Hz, 2H), 8.10-8.17 (m, 1H), 8.64-8.69 (m, 1H), 9.79 (s, 1H), 12.8 (br, 1H). | (ESI+) 492.1 (MH+) | (+) |
| 70 | 2-methyl-4-CF3-5-CO2Et-thiazole | (CDCl3) δ 1.37 (t, J = 7.3 Hz, 3H), 163-1.87 (m, 3H), 1.98-2.22 (m, 3H), 2.36-2.47 (m, 1H), 3.11 (s, 3H), 3.77 (t, J = 7.3 Hz, 1H), 4.38 (q, J = 7.3 Hz, 2H), 4.70-4.94 (m, 2H), 7.50 (d, J = 8.6 Hz, 2H), 7.93 (d, J = 8.6 Hz, 2H), 9.59 (br, 1H). | (ESI+) 555.1 (MH+) | (−) |
| 71 | 2-methyl-4-Me-5-CO2Me-thiazole | (CDCl3) δ 1.63-1.89 (m, 3H), 1.99-2.22 (m, 3H), 2.37-2.48 (m, 1H), 2.59 (s, 3H), 3.08 (s, 3H), 3.68 (t, J = 7.6 Hz, 1H), 3.85 (s, 3H), 4.70-4.93 (m, 2H), 7.42-7.54 (m, 2H), 7.91-7.97 (m, 2H), 8.89 (s, 1H). | (ESI+) 487.1 (MH+) | (−) |
| 72 | 2-methyl-4-Me-5-F-pyridine | (CDCl3) δ 1.67-1.88 (m, 3H), 1.99-2.21 (m, 3H), 2.31 (d, J = 1.2 Hz, 1H), 2.37-2.44 (m, 1H), 3.05 (s, 3H), 3,58 (t, J = 7.6 Hz, 1H), 4.72-4.92 (m, 2H), 7.57 (d, J = 8.6 Hz, 2H), 7.81 (s, 1H), 7.94 (d, J = 8.6 Hz, 2H), 7.97 (s, 1H), 8.08 (d, J = 5.5 Hz, 1H). | (ESI+) 441.2 (MH+) | (−) (DMF) |
| 73 | 6-methyl-3-SO2NMe2-pyridine | (CDCl3) δ 1.67-1.90 (m, 3H), 2.01-2.23 (m, 3H), 2.37-2.45 (m, 1H), 2.72 (s, 6H), 3.07 (s, 3H), 3.67 (t, J = 7.3 Hz, 1H), 4.73-4.94 (m, 2H), 7.59 (d, J = 8.6 Hz, 2H), 7.95 (d, J = 8.6 Hz, 2H), 8.05 (dd, J = 9.2, 2.4 Hz, 1H), 8.19 (s, 1H), 8.36 (d, J = 8.6 Hz, 1H), 8.62 (d, J = 2.4 Hz, 1H). | (ESI+) 516.1 (MH+) | (−) (DMF) |
| 74 | 5-methyl-2-Br-pyrazine | (CDCl3) δ 1.68-1.88 (m, 3H), 2.03-2.22 (m, 3H), 2.37-2.44 (m, 1H), 3.06 (s, 3H), 3,66 (t, J = 7.6 Hz, 1H), 4.73-4.93 (m, 2H), 7.58 (d, J = 8.6 Hz, 2H), 7.80 (s, 1H), 7.96 (d, J = 8.6 Hz, 2H), 8.31 (d, J = 1.8 Hz, 1H), 9.30 (d, J = 1.2 Hz, 1H). | (ESI+) 488.0 (MH+) | (−) (DMF) |

TABLE 13

| No. | structure (A) | 1H NMR (400 MHz) | MS (m/z) | Optical rotation |
|---|---|---|---|---|
| 75 | 5-methyl-2-Ph-pyrazine | (CDCl3) δ 1.68-1.93 (m, 3H), 2.04-2.23 (m, 3H), 2.41-2.48 (m, 1H), 3.07 (s, 3H), 3.69 (t, J = 7.6 Hz, 1H), 4.74-4.93 (m, 2H), 7.42-7.58 (m, 2H), 7.61 (d, J = 8.6 Hz, 2H), 7.86 (s, 1H), 7.95-7.98 (m, 4H), 8.64 (d, J = 1.8 Hz, 1H), 9.54 (s, 1H). | (ESI+) 486.2 (MH+) | (−) (DMF) |
| 76 | 2-methyl-4-CO2Et-oxazole | (d6DMSO) δ 1.33 (t, J = 7.3 Hz, 3H), 1.50-1.83 (m, 3H), 1.86-1.95 (m, 1H), 2.10-2.29 (m, 3H), 3.26 (s, 3H), 3.96 (br, 1H), 4.31 (q, J = 6.7 Hz, 2H), 4.85-5.07 (m, 2H), 7.69 (d, J = 7.9 Hz, 2H), 7.97 (d, J = 7.9 Hz, 2H), 8.60 (s, 1H), 11.9 (s, 1H). | (ESI+) 471.1 (MH+) | (−) |
| 77 | 3-methyl-isoxazolo[4,5-b]pyridine | (d6DMSO) δ 1.59-1.83 (m, 3H), 2.07-2.31 (m, 3H), 2.37-2.46 (m, 1H), 3.28 (s, 3H), 4.77 (t, J = 7.9 Hz, 1H), 4.85-5.08 (m, 2H), 6.44 (t, J = 6.1 Hz, 1H), 7.71 (dd, J = 6.1, 2.4 Hz, 1H), 7.79 (dt, J = 8.6, 1.8 Hz, 2H), 8.01 (dt, J = 8.6, 1.8 Hz, 2H), 8.27 (dd, J = 7.3, 2.4 Hz, 1H), 12.3 (s, 1H). | (ESI+) 450.1 (MH+) | (−) |

TABLE 13-continued

| No. | structure (A) | 1H NMR (400 MHz) | MS (m/z) | Optical rotation |
|---|---|---|---|---|
| 78 | 2-methyl-[1,2,4]triazolo[1,5-a]pyrimidine | (d6DMSO) δ 1.47-1.69 (m, 2H), 1.69-1.78 (m, 1H), 1.80-1.88 (m, 1H), 2.05-2.24 (m, 3H), 3.18 (s, 3H), 4.06 br, 1H), 4.80-5.01 (m, 2H), 7.27 (dd, J = 6.7, 4.3 Hz, 1H), 7.66 (d, J = 8.6 Hz, 2H), 7.90 (d, J = 8.6 Hz, 2H), 8.75 (dd, J = 4.3, 1.8 Hz, 1H), 9.26 (dd, J = 6.7, 1.8 Hz, 1H), 11.4 (s, 1H). | (ESI+) 450.2 (MH+) | (−) (DMF) |
| 79 | 2-methyl-4-(2-hydroxyethyl)thiazole | (d6DMSO) δ 1.43-1.76 (m, 3H), 1.78-1.93 (m, 1H), 1.99-2.27 (m, 3H), 2.70 (t, J = 7.3 Hz, 2H), 3.32 (s, 3H), 3.63 (dd, J = 11.0, 7.3 Hz, 2H), 3.99 (t, J = 7.9 Hz, 1H), 4.59 (t, J = 4.8 Hz, 1H), 4.76-5.02 (m, 2H), 6.78 (s, 1H), 7.63 (d, J = 7.9 Hz, 2H), 7.89 (d, J = 8.6 Hz, 2H), 12.4 (br, 1H). | (ESI+) 459.1 (MH+) | (−) |
| 80 | 2-methyl-6-(2-(dimethylamino)ethoxy)thiazolo[5,4-b]pyridine | (CDCl3) d 1.80-1.90 (m, 2H), 2.02-2.21 (m, 4H), 2.37 (s, 3H), 2.39-2.49 (m, 1H), 2.77 (t, J = 5.5 Hz, 2H), 3.07 (s, 3H), 3.73 (t, J = 7.6 Hz, 1H), 4.49 (t, J = 5.5 Hz, 2H), 4.71-4.93 (m, 2H), 6.78 (d, J = 8.6 Hz, 1H), 7.52 (d, J = 8.6 Hz, 2H), 7.76 (d, J = 8.6 Hz, 1H), 7.93 (d, J = 8.6 Hz, 2H). | (ESI+) 553.2 (MH+) | (−) |

TABLE 14

| No. | structure (A) | 1H NMR (400 MHz) | MS (m/z) | Optical rotation |
|---|---|---|---|---|
| 81 | ethyl 5-methylpyrazine-2-carboxylate | (CDCl3) δ 1.44 (t, J = 7.3 Hz, 3H), 1.66-1.90 (m, 3H), 2.03-2.24 (m, 3H), 2.37-2.46 (m, 1H), 3.07 (s, 3H), 3.72 (t, J = 7.3 Hz, 1H), 4.49 (q, J = 7.3 Hz, 2H), 4.72-4.94 (m, 2H), 7.59 (d, J = 8.6 Hz, 2H), 7.97 (d, J = 8.6 Hz, 2H), 8.11 (s, 1H), 8.94 (d, J = 1.2 Hz, 1H), 9.61 (d, J = 1.2 Hz, 1H). | (ESI+) 482.2 (MH+) | (−) |
| 82 | methyl 5-methylpyrazine-2-carboxylate | (CDCl3) δ 1.65-1.91 (m, 3H), 2.04-2.23 (m, 3H), 2.38-2.46 (m, 1H), 3.07 (s, 3H), 3.71 (t, J = 7.3 Hz, 1H), 4.02 (s, 3H), 4.73-4.94 (m, 2H), 7.59 (dt, J = 8.6, 1.8 Hz, 2H), 7.97 (dt, J = 8.6, 1.8 Hz, 2H), 8.08 (s, 1H), 8.95 (d, J = 1.8 Hz, 1H), 9.60 (d, J = 1.2 Hz, 1H). | (ESI+) 468.2 (MH+) | (−) |
| 83 | 5-cyclopropyl-2-methylpyridine | (CDCl3) δ 0.60-0.70 (m, 2H), 0.94-1.03 (m, 2H), 1.64-1.90 (m, 4H), 1.95-2.23 (m, 3H), 2.34-2.45 (m, 1H), 3.05 (s, 3H), 3.57 (t, J = 7.3 Hz, 1H) 4.68-4.93 (m, 2H), 7.33 (dd, J = 8.6, 1.8 Hz, 1H), 7.54 (d, J = 7.9 Hz, 2H), 7.91 (d, J = 8.6 Hz, 2H), 7.98 (br, 1H), 8.02-8.07 (m, 2H). | (ESI+) 449.2 (MH+) | (−) |
| 84 | 2-cyclopropyl-5-methylpyrazine | (CDCl3) δ 1.02 (d, J = 7.9 Hz, 4H), 1.63-1.90 (m, 3H), 1.95-2.25 (m, 4H), 2.35-2.47 (m, 1H), 3.06 (s, 3H), 3.63 (t, J = 7.6 Hz, 1H), 4.70-4.94 (m, 2H), 7.57 (d, J = 8.6 Hz, 2H), 7.70 (s, 1H), 7.94 (d, J = 8.6 Hz, 2H), 8.09 (d, J = 1.8 Hz, 1H), 9.29 (s, 1H). | (ESI+) 450.2 (MH+) | (−) |
| 85 | 5-acetyl-2,4-dimethylthiazole | (CDCl3) δ 1.64-1.89 (m, 3H), 2.02-2.24 (m, 3H), 2.41 (m, 1H), 2.50 (s, 3H), 2.60 (s, 3H), 3.08 (s, 3H), 3.73 (t, J = 7.6 Hz, 1H), 4.70-4.95 (m, 2H), 7.49-7.55 (m, 2H), 7.92-7.97 (m, 2H), 9.12 (s, 1H). | (ESI+) 471.1 (MH+) | (−) |
| 86 | isopropyl 2-methylbenzothiazole-6-carboxylate | (CDCl3) δ 1.25 (t, J = 7.6 Hz, 1H), 1.41 (d, J = 6.1 Hz, 6H), 1.64-1.89 (m, 3H), 1.97-2.20 (m, 3H), 2.36-2.48 (m, 1H), 3.08 (s, 3H), 3.70 (t, J = 7.3 Hz, 1H), 4.69-4.95 (m, 2H), 5.30 (seq, J = 6.1 Hz, 1H), 7.37 (d, J = 8.6 Hz, 2H), 7.75 (d, J = 8.6 Hz, 1H), 7.88 (d, J = 8.6 Hz, 2H), 8.14 (dd, J = 8.6, 1.2 Hz, 1H), 8.55 (d, J = 1.2 Hz, 1H), 9.75 (s, 1H). | (ESI+) 551.2 (MH+) | (−) |

TABLE 15

| No. | structure (A) | 1H NMR (400 MHz) | MS (m/z) | Optical rotation |
|---|---|---|---|---|
| 87 | 2-methyl-5-(ethylthio)pyridine | (CDCl3) δ 1.26 (t, J = 7.3 Hz, 3H), 1.64-1.91 (m, 3H), 1.95-2.25 (m, 3H), 2.34-2.46 (m, 1H), 2.87 (q, J = 7.3 Hz, 2H), 3.05 (s, 3H), 3.60 (t, J = 7.3 Hz, 1H) 4.70-4.94 (m, 2H), 7.56 (dd, J = 7.9, 1.8 Hz, 2H), 7.11 (dd, J = 8.6, 2.4 Hz, 1H), 7.93 (dd, J = 7.9, 1.8 Hz, 2H), 7.98 (br, 1H), 8.12 (d, J = 9.2 Hz, 1H), 8.22 (d, J = 1.8 Hz, 1H). | (ESI+) 469.2 (MH+) | (−) |
| 88 | 2-methyl-5-(hydroxymethyl)pyridine | (d6DMSO) δ 1.46-1.16 (m, 3H), 1.77-1.87 (m, 1H), 2.02-2.23 (m, 3H), 3.17 (s, 3H), 4.08 (t, J = 7.6 Hz, 1H), 4.44 (d, J = 5.5 Hz, 2H), 4.78-5.00 (m, 2H), 5.21 (t, J = 5.5 Hz, 1H), 7.64-1.70 (m, 3H), 7.89 (d, J = 8.8 Hz, 2H), 8.00 (d, J = 8.6 Hz, 1H), 8.23 (d, J = 1.8 Hz, 1H). | (ESI+) 439.2 (MH+) | (−) |
| 89 | 2-methyl-5-isopropoxypyridine | (CDCl3) d 1.32 (d, J = 6.1 Hz, 6H), 1.63-1.91 (m, 3H), 1.96-2.06 (m, 1H), 2.07-2.23 (m, 2H), 2.35-2.45 (m, 1H), 3.05 (s, 3H), 3.58 (t, J = 7.6 Hz, 1H), 4.69-4.94 (m, 2H), 7.23 (dd, J = 8.7, 2.4 Hz, 1H), 7.57 (d, J = 8.6 Hz, 2H), 7.79 (s, 1H), 7.89 (d, J = 2.4 Hz, 1H), 7.92 (d, J = 8.6 Hz, 2H), 8.08 (d, J = 8.7 Hz, 1H). | (ESI+) 467.2 (MH+) | (−) |
| 90 | 2-methyl-5-ethoxypyridine | (CDCl3) δ 1.41 (t, J = 7.3 Hz, 3H), 1.64-1.91 (m, 3H), 1.95-2.22 (m, 3H), 2.35-2.45 (m, 1H), 3.05 (s, 3H), 3.57 (t, J = 7.9 Hz, 1H), 4.04 (q, J = 7.3 Hz, 2H), 4.70-4.93 (m, 2H), 7.24 (dd, J = 8.6, 3.1 Hz, 1H), 7.56 (d, J = 7.9 Hz, 2H), 7.85-7.95 (m, 4H), 8.09 (d, J = 9.2 Hz, 1H). | (ESI+) 453.2 (MH+) | (−) |
| 91 | 2-methyl-4-(2,2-dimethyl-1,3-dioxolan-4-yl)thiazole (4'RS) | | (ESI+) 515.2 (MH+) | (−) |
| 92 | 2-methyl-4-(2,2-dimethyl-1,3-dioxolan-4-yl)thiazole (4'SR) | | (ESI+) 515.2 (MH+) | (−) |

TABLE 16

| No. | structure (A) | 1H NMR (400 MHz) | MS (m/z) | Optical rotation |
|---|---|---|---|---|
| 93 | 2-methyl-4-(1,2-dihydroxyethyl)thiazole (1'RS) | | (ESI+) 475.1 (MH+) | (−) |
| 94 | 2-methyl-4-(1,2-dihydroxyethyl)thiazole (1'SR) | | (ESI+) 475.2 (MH+) | (−) |
| 95 | 5-methyl-1,2,4-thiadiazole | (CDCl3) δ 1.61-1.91 (m, 3H), 1.99-2.23 (m, 3H), 2.36-2.51 (m, 1H), 3.09 (s, 3H), 3.85 (t, J = 7.3 Hz, 1H), 4.70-4.94 (m, 2H), 7.52 (d, J = 8.6 Hz, 2H), 7.92 (d, J = 8.6 Hz, 2H), 8.32 (s, 1H), 10.4 (brs, 1H). | (ESI+) 416.1 (MH+) | (−) |

TABLE 16-continued

| No. | structure (A) | 1H NMR (400 MHz) | MS (m/z) | Optical rotation |
|---|---|---|---|---|
| 96 | (pyrazine with OMe ether, methyl group) | (CDCl3) δ 1.64-1.91 (m, 3H), 1.98-2.23 (m, 3H), 2.35-2.46 (m, 1H), 3.06 (s, 3H), 3.43 (s, 3H), 3.63 (t, J = 7.3 Hz, 1H), 3.71-3.76 (m, 2H), 4.44-4.50 (m, 2H), 4.70-4.94 (m, 2H), 7.58 (d, J = 7.9 Hz, 2H), 7.70 (brs, 1H), 7.92 (s, 1H), 7.94 (d, J = 8.6 Hz, 2H), 8.96 (d, J = 1.2 Hz, 1H). | (ESI+) 484.2 (MH+) | (−) |
| 97 | (benzothiazole morpholine amide) | (d6DMSO) δ 1.48-1.82 (m, 3H), 1.91-2.02 (m, 1H), 2.03-2.30 (m, 3H), 3.13 (m, 3H), 3.40-3.65 (m, 8H), 4.11 (t, J = 7.3 Hz, 1H), 4.77-5.00 (m, 2H), 7.46 (dd, J = 8.6 Hz, 1H), 7.68 (d, J = 8.6 Hz, 2H), 7.75 (d, J = 7.9 Hz, 1H), 7.91 (d, J = 8.6 Hz, 2H), 8.04 (d, J = 1.2 Hz, 1H), 12.7 (s, 1H). | (ESI+) 578.2 (MH+) | (−) |
| 98 | (pyridine propyl ether, methyl) | (CDCl3) δ 1.03 (t, J = 7.3 Hz, 3H), 1.63-1.91 (m, 5H), 1.96-2.06 (m, 1H), 2.07-2.23 (m, 2H), 2.35-2.46 (m, 1H), 3.05 (s, 3H), 3.57 (t, J = 7.6 Hz, 1H), 3.93 (t, J = 6.4 Hz, 2H), 4.70-4.93 (m, 2H), 7.24 (dd, J = 9.2, 3.1 Hz, 1H), 7.57 (d, J = 8.6 Hz, 2H), 7.82 (s, 1H), 7.88-7.96 (m, 3H), 8.09 (d, J = 9.2 Hz, 1H). | (ESI+) 467.2 (MH+) | (−) |
| 99 | (pyrazine SMe, methyl) | (CDCl3) δ 1.64-1.91 (m, 3H), 1.99-2.24 (m, 3H), 2.36-2.46 (m, 1H), 2.57 (s, 3H), 3.06 (s, 3H), 3.84 (t, J = 7.6 Hz, 1H), 4.71-4.94 (m, 2H), 7.58 (d, J = 8.6 Hz, 2H), 7.66 (s, 1H), 7.95 (d, J = 8.6 Hz, 2H), 8.09 (d, J = 1.2 Hz, 1H), 9.32 (s, 1H). | (ESI+) 456.2 (MH+) | (−) |

REFERENCE EXAMPLE 1

(+)-3-[(1α,3α,4α)-3,4-difluorocyclopentyl]-2-(4-(methylsulfonyl)phenyl)propionic acid As in Example 3, isomer B of (4R)-4-benzyl-3-[3-[(1α,3α,4α)-3,4-difluorocyclopentyl]-2-(4-(methylsulfonyl)phenyl)propanoyl]oxazolidine-2-one (202 mg) was used to afford (+)-3-[(1α,3α,4α)-3,4-difluorocyclopentyl]-2-(4-(methylsulfonyl)phenyl)propionic acid (118 mg).
MS (CI+) m/z: 333 (MH+)
HRMS (CI+) for $C_{15}H_{19}F_2O_4S$ (MH+): calcd, 333.0972. found, 333.0983.

REFERENCE EXAMPLE 2

(+)-3-[(1α,3α,4α)-3,4-difluorocyclopentyl]-2-(4-(methylsulfonyl)phenyl)-N-(thiazole-2-yl)propionamide As in Example 4, (+)-3-[(1α,3α,4α)-3,4-difluorocyclopentyl]-2-(4-(methylsulfonyl)phenyl)propionic acid (90.8 mg) and 2-aminothiazole (67.8 mg) were used to afford (')-3-[(1α,3α,4α)-3,4-difluorocyclopentyl]-2-(4-(methylsulfonyl)phenyl)-N-(thiazole-2-yl)propionamide (104 mg).
MS (EI) m/z: 414 (M+).
HRMS (EI) for $C_{25}H_{27}F_2NO_5S$ (M+): calcd, 414.0883. found, 414.0885.

REFERENCE EXAMPLE 3

(±)-3-[(1β,3α,4α)-3,4-difluorocyclopentyl]-2-(4-(methylsulfonyl)phenyl)propionic acid As in Example 1, 4-methylsulfonylphenylacetic acid (1.04 g) and (1β,3α,4α)-3,4-difluorocyclopentylmethyl iodide (1.20 g) were used to afford (±)-3-[(1β,3α,4α)-3,4-difluorocyclopentyl]-2-(4-(methylsulfonyl)phenyl)propionic acid (1.24 g).

MS (CI+) m/z: 333 (MH+).
HRMS (CI+) for $C_{15}H_{19}F_2O_4S$ (MH+): calcd, 333.0972. found, 333.0986.

REFERENCE EXAMPLE 4

(4R)-4-benzyl-3-[3-[(1β,3α,4α)-3,4-difluorocyclopentyl]-2-(4-(methylsulfonyl)phenyl)propanoyl]oxazolidine-2-one As in Example 2, (±)-3-[(1β,3α,4α)-3,4-difluorocyclopentyl]-2-(4-(methylsulfonyl)phenyl)propionic acid (1.15 g) and (R)-4-benzyloxazolidinone (613 mg) were used to afford a less polar isomer A' (139 mg) and a more polar isomer B' (207 mg) of (4R)-4-benzyl-3-[3-[(1β,3α,4α)-3,4-difluorocyclopentyl]-2-(4-(methylsulfonyl)phenyl)propanoyl]oxazolidine-2-one.
Isomer A':
MS (EI) m/z: 491 (M+).
HRMS (EI) for $C_{25}H_{27}F_2NO_5S$ (M+): calcd, 491.1578. found, 491.1562.
Isomer B':
MS (EI) m/z: 491 (M+).
HRMS (EI) for $C_{25}H_{27}F_2NO_5S$ (M+): calcd, 491.1578. found, 491.1560.

REFERENCE EXAMPLE 5

(−)-3-[(1β,3α,4α)-3,4-difluorocyclopentyl]-2-(4-(methylsulfonyl)phenyl)propionic acid As in Example 3, isomer A' of (4R)-4-benzyl-3-[3-[(1β,3α,4α)-3,4-difluorocyclopentyl]-2-(4-(methylsulfonyl)phenyl)propanoyl]oxazolidine-2-one (150 mg) was used to afford (−)-3-[(1β,3α,4α)-3,4-difluorocyclopentyl]-2-(4-(methylsulfonyl)phenyl)propionic acid (85.9 mg).
MS (CI+) m/z: 333 (MH+).
HRMS (CI+) for $C_{15}H_{19}F_2O_4S$ (MH+): calcd, 333.0972. found, 333.0934.

REFERENCE EXAMPLE 6

(+)-3-[(1β,3α,4α)-3,4-difluorocyclopentyl]-2-(4-(methylsulfonyl)phenyl)propionic acid As in Example 3, isomer B' of (4R)-4-benzyl-3-[3-[(1β,3α,4α)-3,4-difluorocyclopentyl]-2-(4-(methylsulfonyl)phenyl)propanoyl]oxazolidine-2-one (110 mg) was used to afford (+)-3-[(1β,3α,4α)-3,4-difluorocyclopentyl]-2-(4-(methylsulfonyl)phenyl)propionic acid (67.3 mg).

MS (CI$^+$) m/z: 333 (MH$^+$).

HRMS (CI$^+$) for $C_{15}H_{19}F_2O_4S$ (MH$^+$): calcd, 333.0972. found, 333.0952.

REFERENCE EXAMPLE 7

(−)-3-[(1β,3α,4α)-3,4-difluorocyclopentyl]-2-(4-(methylsulfonyl)phenyl)-N-(thiazole-2-yl)propionamide As in Example 4, (−)-3-[(1β,3α,4α)-3,4-difluorocyclopentyl]-2-(4-(methylsulfonyl)phenyl)propionic acid (66.6 mg) and 2-aminothiazole (49.0 mg) were used to afford (−)-3-[(1β,3α,4α)-3,4-difluorocyclopentyl]-2-(4-(methylsulfonyl)phenyl)-N-(thiazole-2-yl)propionamide (60.3 mg).

MS (EI) m/z: 414 (M$^+$).

HRMS (EI) for $C_{25}H_{27}F_2NO_5S$ (M$^+$): calcd, 414.0883. found, 414.0891.

REFERENCE EXAMPLE 8

(+)-3-[(1β,3α,4α)-3,4-difluorocyclopentyl]-2-(4-(methylsulfonyl)phenyl)-N-(thiazole-2-yl)propionamide As in Example 4, (+)-3-[(1β,3α,4α)-3,4-difluorocyclopentyl]-2-(4-(methylsulfonyl)phenyl)propionic acid (45.3 mg) and 2-aminothiazole (33.9 mg) were used to afford (+)-3-[(1β,3α,4α)-3,4-difluorocyclopentyl]-2-(4-(methylsulfonyl)phenyl)-N-(thiazole-2-yl)propionamide (40.6 mg).

MS (EI) m/z: 414 (M$^+$).

HRMS (EI) for $C_{25}H_{27}F_2NO_5S$ (M$^+$): calcd, 414.0883. found, 414.0844.

REFERENCE EXAMPLE 9

(1α,3α,4α)-3,4-difluorocyclopentylmethyl iodide

Step I

[(1α,3β,4β)-3,4-dihydroxycyclopentyl]methyl benzoate (Chemical formula 13)

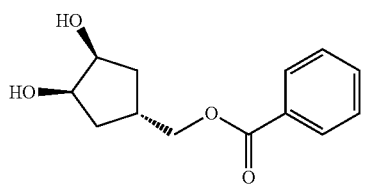

N-methylmorpholine N-oxide (50% aqueous solution, 22.0 mL) and osmium tetraoxide (2.5% t-butanol solution, 1.90 mL) were dissolved in acetone (190 mL). While this solution was being stirred, (3-cyclopentene-1-yl)methyl benzoate (Published Japanese Translation of PCT application No. 7-506816)(20.2 g) in acetone (125 mL) was added dropwise over a time period of 105 min and the mixture was stirred for additional 15 hours at room temperature. Subsequently, chloroform (310 mL) and water (190 mL) were added and the organic layer was separated. The separated organic layer was washed sequentially with 1 mol/L hydrochloric acid (2×90 mL), water (90 mL) and a saturated aqueous sodium bicarbonate solution (60 mL), followed by drying over anhydrous sodium sulfate and concentration under reduced pressure. To the resulting residue, toluene (120 mL) was added and the resulting crystals were collected by filtration to give [(1α,3β,4β)-3,4-dihydroxycyclopentyl]methyl benzoate (16.9 g).

$^1$H NMR (CDCl$_3$) δ 1.71-1.78 (m, 2H), 1.95-2.02 (m, 2H), 2.27 (br, 2H), 2.75-2.87 (m, 1H), 4.19-4.23 (m, 4H), 7.43-7.47 (m, 2H), 7.55-7.59 (m, 1H), 8.01-8.04 (m, 2H).

The filtrate was concentrated under reduced pressure to give a mixture of [(1α,3β,4β)-3,4-dihydroxycyclopentyl]methyl benzoate and [(1β,3β,4β)-3,4-dihydroxycyclopentyl]methyl benzoate (4.23 g, a 1:2 mixture as determined by the integration ratio in $^1$H NMR).

$^1$H NMR (CDCl$_3$) δ 1.58-1.65 (m, 1.3H), 1.71-1.78 (m, 0.7H), 1.96-2.17 (m, 2H), 2.75-2.85 (m, 1H), 4.09-4.32 (m, 4H), 7.42-7.46 (m, 2H), 7.54-7.59 (m, 1H), 8.01-8.06 (m, 2H).

Step II (3aα,5α,6aα)-(tetrahydro-4H-cyclopenta-1,3,2-dioxathiol-5-yl)methyl benzoate S,S-dioxide (Chemical formula 14)

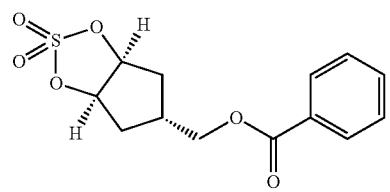

[(1α,3β,4β)-3,4-dihydroxycyclopentyl]methyl benzoate (5.00 g) was suspended in carbon tetrachloride (75 mL). To this suspension, thionyl chloride (1.90 mL) was added and the mixture was refluxed for 1.5 hours under stirring. Subsequently, additional thionyl chloride (0.50 mL) was added and the mixture was refluxed for additional 1 hour under stirring. The reaction mixture was then concentrated under reduced pressure. To the resulting residue, toluene (25 mL) was added and the mixture was concentrated under reduced pressure. Drying the concentrate under reduced pressure gave (3aα,5α,6aα)-(tetrahydro-4H-cyclopenta-1,3,2-dioxathiol-5-yl)methyl benzoate S-oxide (6.09 g). The resulting (3aα,5α,6aα)-(tetrahydro-4H-cyclopenta-1,3,2-dioxathiol-5-yl)methyl benzoate S-oxide (4.27 g), acetonitrile (30 mL) and carbon tetrachloride (30 mL) were mixed together. To this mixture, sodium periodate (6.46 g), ruthenium chloride hydrate (31.3 mg) and water (30 mL) were added and the mixture was stirred at room temperature for 30 min. Subsequently, dichloromethane (50 mL) was added and the insoluble material was removed by filtration. The organic layer of the filtrate was separated and the aqueous layer was extracted with dichloromethane (50 mL). The organic layer and the dichloromethane extracts were combined and washed sequentially with a 1 mol/L aqueous sodium thiosulfate solution (2×40 mL) and water (2×40 mL). The washed organic layer was dried over anhydrous sodium sulfate and concentrated under reduced pressure. The residue was dried under reduced pressure to give (3aα,5α,6aα)-(tetrahydro-4H-cyclopenta-1,3,2-dioxathiol-5-yl)methyl benzoate S,S-dioxide (4.35 g).

MS (CI$^+$) m/z: 299 (MH$^+$).

HRMS (CI$^+$) for $C_{13}H_{15}O_6S$ (MH$^+$): calcd, 299.0589. found, 299.0593.

Step III

[(1α,3α,4β)-3-fluoro-4-hydroxycyclopentyl]methyl benzoate

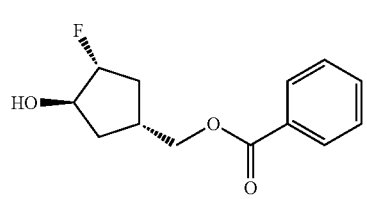

(Chemical formula 15)

Tetrabutylammonium fluoride hydrate (571 mg) was dissolved in dehydrated acetonitrile (5 mL) and the solution was concentrated under reduced pressure. This was repeated two more times and the residue was dried at 40° C. for 45 min under reduced pressure. The resulting residue was dissolved in dehydrated acetonitrile (5 mL) and (3aα,5α,6aα)-(tetrahydro-4H-cyclopenta-1,3,2-dioxathiol-5-yl)methyl benzoate S,S-dioxide (500 mg) was added. This reaction mixture was refluxed for 45 min under stirring and then concentrated under reduced pressure. The residue was dissolved in ethanol (5 mL) and sulfuric acid (0.15 mL) was added. The mixture was again refluxed for 10 min under stirring and concentrated under reduced pressure. The reside was dissolved in ethyl acetate (40 mL) and the solution was washed sequentially with a saturated sodium bicarbonate solution (5 mL) and a saturated sodium chloride solution (5 mL), dried over anhydrous sodium sulfate, and concentrated under reduced pressure. The resulting residue was purified by a silica gel column (eluant:hexane/ethyl acetate=1:1) to give [(1α,3α,4β)-3-fluoro-4-hydroxycyclopentyl]methyl benzoate (342 mg).

MS (EI) m/z: 238 (M$^+$).

HRMS (EI) for $C_{13}H_{15}FO_3$(M$^+$): calcd, 238.1005. found, 238.1046.

Step IV

[(1α,3α,4α)-3,4-difluorocyclopentyl]methyl benzoate

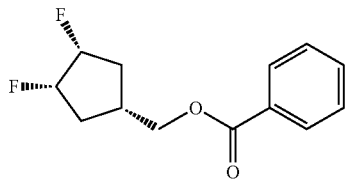

(Chemical formula 16)

[(1α,3α,4β)-3-fluoro-4-hydroxycyclopentyl]methyl benzoate (326 mg) was dissolved in dehydrated tetrahydrofuran (5 mL). To this solution, bis(2-methoxyethyl)aminosulfur trifluoride (455 mg) in dehydrated tetrahydrofuran (2 mL) was added and the mixture was refluxed for 1.5 hours under stirring. Subsequently, the reaction mixture was poured into a saturated aqueous sodium bicarbonate solution (10 mL) and the mixture was extracted with ethyl acetate (2×30 mL). The ethyl acetate extracts were combined, washed with a saturated sodium chloride solution (2×10 mL), dried over anhydrous sodium sulfate, and concentrated under reduced pressure. The resulting residue was purified by a silica gel column (eluant:hexane/ethyl acetate=4:1) to give [(1α,3α,4α)-3,4-difluorocyclopentyl]methyl benzoate (233 mg).

MS (CI$^+$) m/z: 241 (MH$^+$).

HRMS (CI$^+$) for $C_{13}H_{15}F_2O_2$(MH$^+$): calcd, 241.1040. found, 241.1043.

Step V

[(1α,3α,4α)-3,4-difluorocyclopentyl]methanol

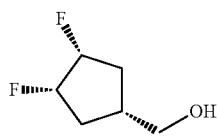

(Chemical formula 17)

[(1α,3α,4α)-3,4-difluorocyclopentyl]methyl benzoate (221 mg) was dissolved in ethanol (3 mL). To this solution, an aqueous solution (1 mL) of potassium carbonate (191 mg) was added and the mixture was refluxed for 4 hours under stirring. Subsequently, the reaction mixture was concentrated under reduced pressure and the resulting residue was purified by a silica gel column (eluant:hexane/ethyl acetate=1:2) to give [(1α,3α,4α)-3,4-difluorocyclopentyl]methanol (123 mg).

MS (CI$^+$) m/z: 137 (MH$^+$).

HRMS (CI$^+$) for $C_6H_{11}F_2O$ (MH$^+$): calcd, 137.0778. found, 137.0801.

Step VI (1α,3α,4α)-3,4-difluorocyclopentylmethyl iodide

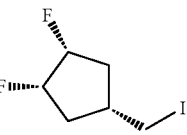

(Chemical formula 18)

Iodine (120 mg) was added to a solution of imidazole (64.5 mg) and triphenylphosphine (124 mg) in dichloromethane (2.0 mL) under cooling with ice. The mixture was stirred at room temperature for 30 min. Subsequently, [(1α,3α,4α)-3,4-difluorocyclopentyl]methanol (43.0 mg) in dichloromethane (0.5 mL) was added and the mixture was stirred at room temperature for additional 4 hours. The insoluble material was removed by filtration and the filtrate was concentrated. Purification of the resulting residue by silica gel column chromatography afforded (1α,3α,4α)-3,4-difluorocyclopentylmethyl iodide (28.0 mg).
MS (EI) m/z: 246 (M⁺).
HRMS (EI) for $C_6H_9F_2I$ (M⁺): calcd, 245.9717. found, 245.9741.

REFERENCE EXAMPLE 10

(1β,3α,4α)-3,4-difluorocyclopentylmethyl iodide

Step I (3aα,5β,6aα)-(tetrahydro-4H-cyclopenta-1,3,2-dioxathiol-5-yl)methyl benzoate S,S-dioxide A mixture (4.23 g) of [(1α,3β,4β)-3,4-dihydroxycyclopentyl]methyl benzoate and [(1β,3β,4β)-3,4-dihydroxycyclopentyl]methyl benzoate obtained in Step I of Reference Example 9 was mixed with carbon tetrachloride (75 mL). To this mixture, thionyl chloride (2.00 mL) was added and the mixture was refluxed for 30 min under stirring. Subsequently, the reaction mixture was concentrated under reduced pressure. Toluene (75 mL) was added to the residue and the mixture was again concentrated under reduced pressure. The residue was dried under reduced pressure. The dried residue was mixed with acetonitrile (35 mL) and carbon tetrachloride (35 mL). This was followed by the addition of sodium periodate (7.66 g), ruthenium chloride hydrate (37.1 mg) and water (35 mL) and mixing at room temperature for 30 min. Subsequently, dichloromethane (60 mL) was added and the insoluble material was removed by filtration. The organic layer of the filtrate was separated and the aqueous layer was extracted with dichloromethane (60 mL). The organic layer and the dichloromethane extracts were combined. The combined organic layer was washed sequentially with a 1 mol/L aqueous solution of sodium thiosulfate (2×50 mL) and water (2×50 mL), dried over anhydrous sodium sulfate and concentrated under reduced pressure. The resulting residue was purified by a silica gel column (eluant:hexane/ethyl acetate=1:1) to give (3aα,5β,6aα)-(tetrahydro-4H-cyclopenta-1,3,2-dioxathiol-5-yl)methyl benzoate S,S-dioxide (2.43 g) and (3aα,5α,6aα)-(tetrahydro-4H-cyclopenta-1,3,2-dioxathiol-5-yl)methyl benzoate S,S-dioxide (1.33 g).
MS (EI) m/z: 298 (M⁺).
HRMS (EI) for $C_{13}H_{14}O_6S$ (M⁺): calcd, 298.0511. found, 298.0493.

Step II

[(1β,3α,4β)-3-fluoro-4-hydroxycyclopentyl]methyl benzoate

Using (3aα,5β,6aα)-(tetrahydro-4H-cyclopenta-1,3,2-dioxathiol-5-yl)methyl benzoate S,S-dioxide (1.00 g), the reaction was carried out as in Step III of Reference Example 9 to afford [(1β,3α,4β)-3-fluoro-4-hydroxycyclopentyl]methyl benzoate (660 mg).
MS (CI⁺) m/z: 239 (MH⁺).
HRMS (CI⁺) for $C_{13}H_{16}FO_3$(MH⁺): calcd, 239.1083. found, 239.1040.

Step III

[(1β,3α,4α)-3,4-difluorocyclopentyl]methyl benzoate

Using [(1β,3α,4β)-3-fluoro-4-hydroxycyclopentyl]methyl benzoate (644 mg), the reaction was carried out as in Step IV of Reference Example 9 to afford [(1β,3α,4α)-3,4-difluorocyclopentyl]methyl benzoate (365 mg).
MS (CI⁺) m/z: 241 (MH⁺).
HRMS (CI⁺) for $C_{13}H_{15}F_2O_2$(MH⁺): calcd, 241.1040. found, 241.1012.

Step IV

[(1β,3α,4α)-3,4-difluorocyclopentyl]methanol

Using [(1β,3α,4α)-3,4-difluorocyclopentyl]methyl benzoate (349 mg), the reaction was carried out as in Step V of Reference Example 9 to afford [(1β,3α,4α)-3,4-difluorocyclopentyl]methanol (184 mg).
MS (CI⁺) m/z: 137 (MH⁺).
HRMS (CI⁺) for $C_6H_{11}F_2O$ (MH⁺): calcd, 137.0778. found, 137.0754.

Step V (1β,3α,4α)-3,4-difluorocyclopentylmethyl iodide

Using (1β,3α,4α)-3,4-difluorocyclopentyl]methanol (3.46 g), the reaction was carried out as in Step VI of Reference Example 9 to afford (1β,3α,4α)-3,4-difluorocyclopentylmethyl iodide (4.72 g).
MS (EI) m/z: 246 (M⁺).
HRMS (EI) for $C_6H_9F_2I$ (M⁺): calcd, 245.9717. found, 245.9749.

TEST EXAMPLE 1

GK Activity Test

GK activity was determined by measuring the amount of NADH produced in a conjugation reaction catalyzed by glucose-6-dehydrogenase, rather than directly measuring the amount of glucose-6-phosphate produced in the reaction catalyzed by glucokinase.
(Preparation of Recombinant GK)
Cloning Human Hepatic or Pancreatic Glucokinases and their Recombinant Proteins
Based on the sequence of human hepatic GK (GenBank Accession Number: NM_033507) and the sequence of human pancreatic GK (GenBank Accession Number: NM_000162), PCRs were performed using Pyrobest DNA polymerase (TaKaRa) and using human hepatic cDNA (Clontech) and human pancreatic cDNA (Clontech) as templates. The cloned genes were expressed in E. coli in soluble fractions as His-tagged fusion proteins that are 6×His-tagged at the C-terminal. The cells were lysed by sonication and the lysate was centrifuged and the supernatant collected. The supernatant was subjected to purification by metal chelate affinity chromatography.
The purified enzyme was stored at −80° C. in a HEPES buffer (pH 7.3) containing 12.5 mM HEPES, 75 mM KCl, 0.5 mM $MgCl_2$, 0.5 mM DTT, 2.5 mM glucose and 50% Glycerol.
(GK Activity Assay)
The GK activity was assayed using a half-area 96-well flat-bottom plate (Costar) at 25° C. The incubation mixture was prepared to contain 25 mM HEPES buffer (pH 7.1) (Invitrogen), 25 mM KCl (Wako Pure Chemical Industries), 2 mM $MgCl_2$ (Wako Pure Chemical Industries), 5 mM D-glucose (Wako Pure Chemical Industries), 1 mM ATP (Roche), 1 mM NAD (Sigma), 1 mM dithiothreitol (Wako Pure Chemical Industries), 5 Units/mL G6PDH (Sigma), 0.1% BSA (Sigma), and a test compound or 5% DMSO, and GK.

Each test compound was dissolved in DMSO. 2 μL of this solution was added to 20 μL of a solution containing HEPES buffer (pH 7.1), KCl, MgCl$_2$, D-glucose, ATP, NAD and dithiothreitol. 18 μL of a solution containing G6PDH, BSA and recombinant GK was then added to initiate the reaction. GK was added so that the increase in the absorbance was 0.002 to 0.003 in one minute in the presence of 5% DMSO. Using a SPECTRAmax190 microplate spectrophotometer (Molecular Device), the increase in the absorbance at 340 nm was measured for 15 min after the reaction had been started. The increase measured in the first 10 minutes was used to evaluate the activity.

It turned out that the hepatic GK activity increased to 150% or more in the presence of 10 μM of Compound No. 11 or No. 14 and to 200% or more in the presence of 10 μM of any of Compounds No. 1 to No. 10, No. 12, No. 13, No. 15 to No. 17, No. 20, No. 21, No. 23, No. 25, No. 27, No. 30, No. 31, No. 33 to No. 36, No. 43 to No. 46, No. 48, No. 50, No. 54, No. 55, No. 60, No. 61, No. 68, No. 69, No. 71, No. 73 to No. 75, and No. 79 to No. 82, relative to the hepatic GK activity observed for the well containing none of these compounds.

TEST EXAMPLE 2

Hypoglycemic Activity Test

Using male 7- to 9-week-old ICR mice (Charles River Laboratories Japan), the effect of each test compound on the blood glucose levels was observed. Specifically, each compound was dissolved in a 60:40 mixture of Gelucire44/14 (Gatefosse) and PEG400 and was orally administered to the animals after a 2-hour fasting period (30 mg/kg, 10 mL/kg). Using a tube coated with dipotassium ethylenediamine tetraacetate, blood samples were collected from the tail vein immediately before administration (Pre-value), and 0.5, 2 and 4 hours after administration. The blood samples were centrifuged (4° C., 3,600 g, 3 min) to obtain plasma samples.

Each sample was diluted 5-fold with physiological saline and the blood glucose level was measured using glucose CII-test Wako (Wako Pure Chemical Industries). 10 μL each of one of the samples, physiological saline and a 100 mg/dL standard glucose solution (200 mg/dL standard glucose solution diluted two-fold with physiological saline) were placed in each well of a 96-well flat plate. 150 μL of a color-forming solution was added to each well and the plate was left at 37° C. for 5 min to allow the solution to develop color. Using a Lucy2 luminescence reader (Aloka), the measurements were taken at OD=492 nm. The decrease in the sigma glucose (mean decrease in the glucose levels at each blood collection point relative to the Pre-value) was determined from the decrease in the glucose level at each blood collection point relative to the Pre-value.

It was demonstrated that the decrease in the sigma glucose level was 30% or more for each of Compounds No. 1, No. 2, No. 3, No. 17, No. 27, No. 30, No. 35, No. 36, No. 46, No. 54, No. 55 and No. 74, whereas none of Reference Compounds No. 2, No. 7 and No. 8 resulted in a sigma glucose decrease higher than 15%.

TEST EXAMPLE 3

In Vivo Pharmacokinetics Test

Using male 6-week-old ICR mice (Charles River Laboratories Japan), the oral bioavailability of each test compound was evaluated. Specifically, each test compound was dissolved in dimethylsulfoxide (DMSO, Sigma) and the solution was added to a 1/15 M aqueous solution of sodium dihydrogen phosphate (Wako Pure Chemical Industries) to a concentration of 200 μM. DMSO was added to a final concentration of 30%. The resulting solution was administered to animals. As an intravenous injection group, a group of ICR mice, fasted overnight, were injected in their tail veins with the test compound solution (1 μmol/kg, 5 mL/kg). 5, 15 and 30 minutes after and 1, 2, 4, 8 and 24 hours after the intravenous administration, blood samples were collected from the eyeground of each animal using a heparin-coated capillary tube. The blood samples were centrifuged to obtain plasma samples. As an oral administration group, a group of mice were forcibly orally administered the same solution (2 μmol/kg, 10 mL/kg). Blood samples were collected from the eyeground 15 and 30 minutes after and 1, 2, 4, 8 and 24 hours after the oral administration and were centrifuged to obtain plasma samples. 10 μL of the separated plasma was diluted with 100 μL of physiological saline and 10 μL of dimethylsulfoxide (sigma) and analyzed by a liquid chromatography-equipped triple quadrupole mass spectrometer (API-3000, Applied Biosystems) for the plasma concentration of unchanged product. The area under the plasma concentration-time curve (AUC) was determined by the trapezoidal method. The bioavailability of a test compound was determined by dividing the average AUC of the oral administration group corrected for the dose by the average AUC of the intravenous administration group. Compound No. 1 showed 50% or higher bioavailability.

TEST EXAMPLE 4

In Vitro Liver Microsome Metabolic Stability Test (Method 1)

In a glass test tube, each test compound was incubated with a solution containing liver microsomes of human (Xenotech) or murine (originally prepared from male 7-week-old ICR mice; Charles River Laboratories Japan) origin at 37° C. for 5 min to evaluate the metabolic stability of the compound. The incubation mixture contained 100 mM potassium phosphate buffer (pH 7.4, Wako Pure Chemical Industries), 3 mM MgCl$_2$ (Wako Pure Chemical Industries), 5 mM glucose-6-phosphate (Roche), 1 mM EDTA (Tokyo Chemical Industry), 1 I.U. glucose 6-phosphate dehydrogenase (Roche) and 1 mg/mL liver microsome. A test compound was dissolved in DMSO and the solution was added to the reaction mixture to a final concentration of 1 μM. The metabolic process was initiated by the addition of an NADPH (Roche) solution to a final concentration of 1 mM and was terminated after 5 min by the addition of an equal volume of acetonitrile (Fischer). After termination of the process, the supernatant was separated by centrifugation and analyzed by a liquid chromatography-equipped mass spectrometer (SHIMADZU 2010A, Shimadzu) for the concentration of unchanged product. The metabolic clearance in both humans and mice was 0.06 mL/min/mg protein or lower for each of Compounds No. 1, No. 2 and No. 3.

(Method 2)

In a glass test tube, each test compound was incubated with a solution containing liver microsomes of human (Xenotech) or murine (originally prepared from male 7-week-old ICR mice; Charles River Laboratories Japan) origin at 37° C. for 25 min to evaluate the metabolic stability of the compound. The incubation mixture contained 100 mM potassium phosphate buffer (pH 7.4, Wako Pure Chemical Industries), 3 mM MgCl$_2$ (Wako Pure Chemical Industries), 5 mM glucose-6-phosphate (Roche), 1 mM EDTA (Tokyo Chemical Industry), 1 I.U. glucose 6-phosphate dehydrogenase (Roche) and 0.2 mg/mL liver microsome. A test compound was dissolved in DMSO and the solution was added to the reaction mixture to a final concentration of 1 μM. The metabolic process was initiated by the addition of an NADPH (Roche) solution to a final concentration of 1 mM and was terminated after 25 min by the addition of an equal volume of acetonitrile (Fischer). After termination of the process, the supernatant was separated by centrifugation and analyzed by a liquid chromatography-equipped mass spectrometer (SHIMADZU 2010A, Shimadzu) for the concentration of unchanged product. The metabolic clearance in both humans and mice was 0.05 mL/min/mg protein or lower for each of Compounds No. 1, No. 17, No. 27, No. 30, No. 35, No. 36 and No. 46.

INDUSTRIAL APPLICABILITY

The compounds of the present invention act as effective GK activators or hypoglycemic agent and cause fewer side effect (such as prolongation of QT interval and hypoglycemia) and are useful in the treatment or prevention of diabetes, obesity and other disorders.

The invention claimed is:

1. A compound represented by the following formula (1), or a pharmaceutically acceptable salt thereof:

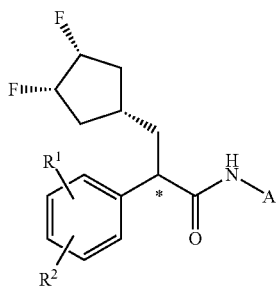

(1)

(wherein the carbon atom denoted by * is in the R-configuration; $R^1$ and $R^2$ are each independently a hydrogen atom, a halogen atom, an amino group, a hydroxyl group, a hydroxyamino group, a nitro group, a cyano group, a sulfamoyl group, a $C_1$-$C_6$ alkyl group, a $C_1$-$C_6$ alkoxy group, a $C_1$-$C_6$ alkylsulfanyl group, a $C_1$-$C_6$ alkylsulfinyl group or a $C_1$-$C_6$ alkylsulfonyl group; and A is a substituted or unsubstituted heteroaryl group).

2. The compound according to claim 1, or a pharmaceutically acceptable salt thereof, wherein $R^1$ is a hydrogen atom and $R^2$ is a $C_1$-$C_6$ alkylsulfonyl group.

3. The compound according to claim 1, or a pharmaceutically acceptable salt thereof, wherein $R^1$ is a hydrogen atom and $R^2$ is a methylsulfonyl group.

4. The compound according to claim 1 represented by the following formula (1a), or a pharmaceutically acceptable salt thereof:

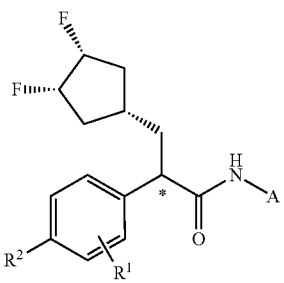

(1a)

(wherein *, $R^1$, $R^2$ and A are as defined in claim 1).

5. The compound according to claim 1 represented by the following formula (1b), or a pharmaceutically acceptable salt thereof:

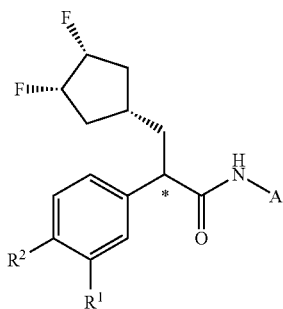

(1b)

(wherein *, $R^1$, $R^2$ and A are as defined in claim 1).

6. The compound according to claim 1, or a pharmaceutically acceptable salt thereof, wherein A is a heteroaryl group that is unsubstituted or monosubstituted with a halogen atom, a $C_1$-$C_6$ alkyl group, a $C_1$-$C_6$ alkoxy group, a nitro group, a cyano group or —$(CH_2)_m C(O)OR^3$ (wherein $R^3$ is a hydrogen atom or a $C_1$-$C_6$ alkyl group, and m is an integer of 0 to 2).

7. The compound according to claim 1, or a pharmaceutically acceptable salt thereof, wherein A is a heteroaryl group unsubstituted or monosubstituted with a halogen atom or a $C_1$-$C_6$ alkyl group.

8. The compound according to claim 6, or a pharmaceutically acceptable salt thereof, wherein A is a unsubstituted or monosubstituted heteroaryl group which is a 5- or 6-membered aromatic heterocyclic ring that contains 1 to 3 heteroatoms selected from the group consisting of a sulfur atom, an oxygen atom and a nitrogen atom, one of which is a nitrogen atom adjacent to a ring-linking atom.

9. The compound according to claim 6, or a pharmaceutically acceptable salt thereof, wherein A is a unsubstituted or monosubstituted heteroaryl group which is a fused heterocyclic ring containing a 5- or 6-membered aromatic heterocyclic ring that contains 1 to 3 heteroatoms selected from the group consisting of a sulfur atom, an oxygen atom and a nitrogen atom, one of which is a nitrogen atom adjacent to a ring-linking atom.

10. The compound according to claim 6, or a pharmaceutically acceptable salt thereof, wherein A is a unsubstituted or monosubstituted heteroaryl group which is selected from the following:

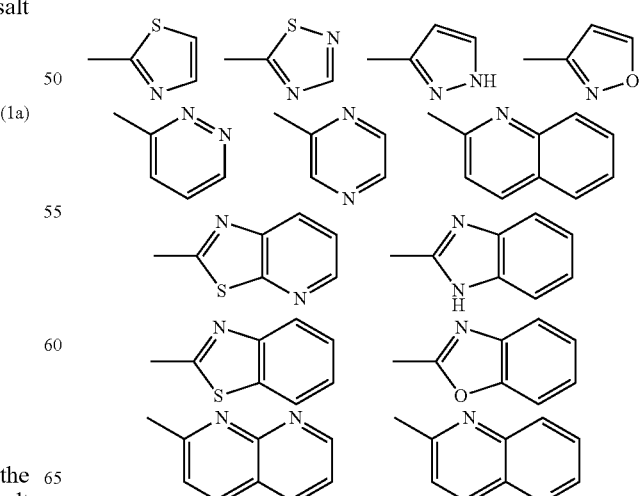

-continued

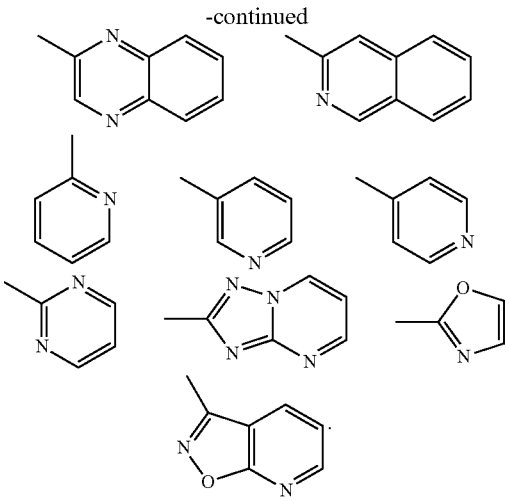

11. (R)-3-((1r, 3R, 4S)-3,4-difluorocyclopentyl)-2-(4-(methylsulfonyl)phenyl)-N-(thiazole-2-yl)propionamide, (R)-3-((1r, 3R, 4S)-3,4-difluorocyclopentyl)-2-(4-(methylsulfonyl)phenyl)-N-(5-fluorothiazole-2-yl)propionamide, (R)-3-((1r, 3R, 4S)-3,4-difluorocyclopentyl)-2-(4-(methylsulfonyl)phenyl)-N-(1-methylpyrazole-3-yl)propionamide, (R)-3-((1r, 3R, 4S)-3,4-difluorocyclopentyl)-2-(4-(methylsulfonyl)phenyl)-N-(pyrido[3,2-d]thiazole-2-yl)propionamide or (R)-3-((1r, 3R, 4S)-3,4-difluorocyclopentyl)-2-(4-(methylsulfonyl)phenyl)-N-(3-methylthiadiazole-5-yl) propionamide, or a pharmaceutically acceptable salt thereof.

12. (−)-3-[(1α,3α,4α)-3,4-difluorocyclopentyl]-2-(4-(methylsulfonyl)phenyl)-N-(thiazole-2-yl)propionamide, or a pharmaceutically acceptable salt thereof.

13. (−)-3-[(1α,3α,4α)-3,4-difluorocyclopentyl]-2-(4-(methylsulfonyl)phenyl)-N-(5-fluorothiazole-2-yl)propionamide, or a pharmaceutically acceptable salt thereof.

14. (−)-3-[(1α,3α,4α)-3,4-difluorocyclopentyl]-2-(4-(methylsulfonyl)phenyl)-N-(1-methylpyrazole-3-yl)propionamide, or a pharmaceutically acceptable salt thereof.

15. (−)-3-[(1α,3α,4α)-3,4-difluorocyclopentyl]-2-(4-(methylsulfonyl)phenyl)-N-(pyrido[3,2-d]thiazole-2-yl)propionamide, or a pharmaceutically acceptable salt thereof.

16. (−)-3-[(1α,3α,4α)-3,4-difluorocyclopentyl]-2-(4-(methylsulfonyl)phenyl)-N-(3-methylthiadiazole-5-yl)propionamide, or a pharmaceutically acceptable salt thereof.

17. A method of treating diabetes, comprising administering the compound according to claim 1 or a pharmaceutically acceptable salt thereof.

18. A pharmaceutical composition comprising the compound according to claim 1 or a pharmaceutically acceptable salt thereof and a pharmaceutically acceptable carrier.

19. A method of treating diabetes, comprising administering the compound according to claim 11 or a pharmaceutically acceptable salt thereof.

20. A method of treating diabetes, comprising administering the compound according to claim 12 or a pharmaceutically acceptable salt thereof.

21. A method of treating or preventing diabetes, comprising administering the compound according to claim 13 or a pharmaceutically acceptable salt thereof.

22. A method of treating or preventing diabetes, comprising administering the compound according to claim 14 or a pharmaceutically acceptable salt thereof.

23. A method of treating diabetes, comprising administering the compound according to claim 15 or a pharmaceutically acceptable salt thereof.

24. A method of treating diabetes, comprising administering the compound according to claim 16 or a pharmaceutically acceptable salt thereof.

25. A pharmaceutical composition comprising the compound according to claim 11 or a pharmaceutically acceptable salt thereof and a pharmaceutically acceptable carrier.

26. A pharmaceutical composition comprising the compound according to claim 12 or a pharmaceutically acceptable salt thereof and a pharmaceutically acceptable carrier.

27. A pharmaceutical composition comprising the compound according to claim 13 or a pharmaceutically acceptable salt thereof and a pharmaceutically acceptable carrier.

28. A pharmaceutical composition comprising the compound according to claim 14 or a pharmaceutically acceptable salt thereof and a pharmaceutically acceptable carrier.

29. A pharmaceutical composition comprising the compound according to claim 15 or a pharmaceutically acceptable salt thereof and a pharmaceutically acceptable carrier.

30. A pharmaceutical composition comprising the compound according to claim 16 or a pharmaceutically acceptable salt thereof and a pharmaceutically acceptable carrier.

* * * * *